United States Patent [19]

Hayase et al.

[11] Patent Number: 5,185,342
[45] Date of Patent: Feb. 9, 1993

[54] ALKOXYIMINOACETAMIDE DERIVATIVES AND THEIR USE AS FUNGICIDES

[75] Inventors: Yoshio Hayase, Kameyama, Japan; Takahiro Kataoka, Clayton, Mo.; Hideyuki Takenaka, Shiga, Japan; Mitsuhiro Ichinari, Shiga, Japan; Michio Masuko, Koga, Japan; Toshio Takahashi, Nishinomiya, Japan; Norihiko Tanimoto, Shiga, Japan

[73] Assignee: Shionogi Seiyaku Kabushiki Kaisha, Osaka, Japan

[21] Appl. No.: 524,056

[22] Filed: May 16, 1990

[30] Foreign Application Priority Data

May 17, 1989 [JP] Japan .................. 1-124059
Dec. 29, 1989 [JP] Japan .................. 1-341175

[51] Int. Cl.$^5$ .................. A61K 31/505; A61K 31/34; A01N 37/18; A01N 43/16; C07D 239/02; C07D 401/02; C07D 277/02; C07C 321/00
[52] U.S. Cl. .................. 514/274; 514/63; 514/269; 514/312; 514/333; 514/335; 514/336; 514/338; 514/346; 514/367; 514/459; 514/461; 514/618; 514/619; 544/229; 544/296; 544/316; 544/317; 546/14; 546/153; 546/157; 546/256; 546/261; 546/270; 546/283; 548/110; 548/157; 548/171; 549/214; 549/414; 549/415; 549/419; 549/473; 549/496; 564/147; 564/162; 564/165
[58] Field of Search .............. 544/316, 229, 296, 298, 544/317; 546/152, 290, 14, 157, 153, 256, 261; 564/147, 162, 165; 549/551, 214, 414, 415, 419, 473, 496; 548/110, 157, 171; 514/63, 269, 274, 312, 333, 335, 338, 336, 367, 346, 459, 461, 618, 619

[56] References Cited

U.S. PATENT DOCUMENTS 3,219,694  11/1965  Yates .................. 564/74

FOREIGN PATENT DOCUMENTS 0023891  2/1981  European Pat. Off. .
0253213  1/1988  European Pat. Off. .
0253213  1/1988  European Pat. Off. .
0254426  1/1988  European Pat. Off. .
0289382  1/1989  European Pat. Off. .

*Primary Examiner*—John M. Ford
*Assistant Examiner*—Y. N. Gupta
*Attorney, Agent, or Firm*—Wenderoth, Lind & Ponack

[57] ABSTRACT

A fungicidal composition for agricultural use, which comprises a compound of the formula:

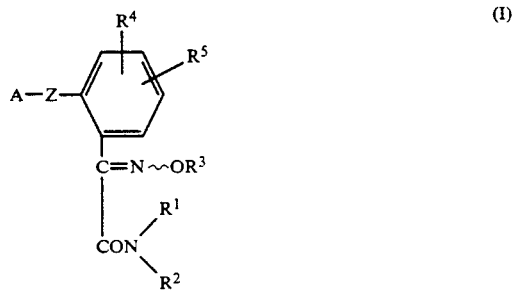

wherein $R^1$ and $R^2$ are each hydrogen, lower alkyl or cyclo(lower)alkyl; $R^3$ is lower alkyl or cyclo(lower)alkyl; $R^4$ and $R^5$ are each hydrogen, lower alkyl, lower alkoxy, halogen-substituted lower alkyl, lower alkyl-substituted silyl, halogen or nitro; A represents an unsaturated hydrocarbon group, a halogen-substituted unsaturated hydrocarbon group, a phenyl group or a heterocyclic group, among which the phenyl group and the heterocyclic group may be optionally substituted with not more than three substituents; and Z is —CH$_2$—, —CH(OH)—, —CO—, —O—, —S—, —NR— (R being hydrogen or lower alkyl), —CH$_2$CH$_2$—, —CH=CH—, —CH$_2$O—, —CH$_2$S—, —CH$_2$SO—, —OCH$_2$—, —SCH$_2$— or —SOCH$_2$—.

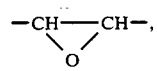

20 Claims, No Drawings

ALKOXYIMINOACETAMIDE DERIVATIVES AND THEIR USE AS FUNGICIDES

The present invention relates to alkoxyiminoacetamide derivatives and their use as fungicides, particularly in the agricultural field.

Various alkoxyiminoacetic acid derivatives having a diaryl ether group are known to exert biological activities including fungicidal activity, herbicidal activity, etc. For instance, some phenoxyphenylalkoxyiminoacetic esters are disclosed to exert fungicidal activity in JP-A-63-23852 and JP-A-63-30463, some phenoxyphenylalkoxyiminoacetamides are disclosed to have herbicidal activity in JP-A-55-35006 and JP-A-56-29560, and some pyridyloxyphenyl-alkoxyiminoacetamides are disclosed to show herbicidal activity in JP-A-56-55368. However, the relationship between chemical structure and biological activity has not sufficiently been clarified so that it is still hardly possible to predict the biological activity to be exerted by a chemical compound from its chemical structure.

As the result of an extensive study on alkoxyiminoacetic acid derivatives having a diaryl ether group, it has been found that a group of alkoxyiminoacetamides of the following formula show a strong fungicidal activity against a wide variety of fungi, particularly phytopathogenic fungi:

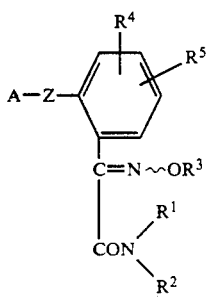
(I)

wherein $R^1$ and $R^2$ are each hydrogen, lower alkyl or cyclo(lower)alkyl; $R^3$ is lower alkyl or cyclo(lower)alkyl; $R^4$ and $R^5$ are each hydrogen, lower alkyl, lower alkoxy, halogen-substituted lower alkyl, lower alkyl-substituted silyl, halogen or nitro; A represents an unsaturated hydrocarbon group, a halogen-substituted unsaturated hydrocarbon group, a phenyl group or a heterocyclic group, among which the phenyl group and the heterocyclic group may be optionally substituted with not more than three substituents; and Z is —$CH_2$—, —CH(OH)—, —CO—, —O—, —S—, —NR— (R being hydrogen or lower alkyl), —$CH_2CH_2$—, —CH=CH—,

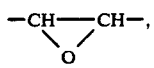

—$CH_2O$—, —$CH_2S$—, —$CH_2SO$—, —$OCH_2$—, —$SCH_2$— or —$SOCH_2$—.

In this specification, the term "lower" is generally used to mean a group having not more than 8 carbon atoms, preferably not more than 6 carbon atoms. Particularly, the term "lower alkyl" can cover an alkyl group having not more than 6 carbon atoms, preferably not more than 4 carbon atoms (e.g. methyl, ethyl, propyl, isopropyl, butyl, isobutyl, t-butyl). The term "cyclo(lower)alkyl" can cover a cycloalkyl group having 3 to 8 carbon atoms, preferably 3 to 6 carbon atoms (e.g. cyclopropyl, cyclopentyl, cyclohexyl). The term "lower alkoxy" can cover an alkoxy group having not more than 6 carbon atoms, preferably not more than 4 carbon atoms (e.g. methoxy, ethoxy, propoxy, isopropoxy, butoxy). The term "lower alkenyl" refers to an alkenyl group having 2 to 8 carbon atoms, preferably 3 to 6 carbon atoms (e.g. allyl, isopropenyl, butenyl, isobutenyl, pentenyl, hexenyl, hexadienyl).

The term "halogen" covers chlorine, bromine, iodine and fluorine. The terms "halogen-substituted", "lower alkyl-substituted" represents any group substituted with not more than three halogen atoms or lower alkyl groups.

The unsaturated hydrocarbon group represented by the symbol A can mean an alkenyl or alkadienyl group having 2 to 12 carbon atoms, preferably 3 to 10 carbon atoms. The heterocyclic group represented by the symbol A may cover a 5- to 7-membered, heteromonocyclic group having not more than three ring nitrogen atoms, and its specific examples are pyridine, pyrimidine, pyridazine, etc. When said phenyl or heterocyclic group is substituted, the substituent(s) may be one to three chosen from lower alkyl, lower alkanoyl, lower alkyl-substituted silyl, halogen-substituted alkyl, di(lower)alkylamino, phenyl, phenyl(lower)alkyl, phenyl(lower)alkenyl, furyl(lower)alkyl, furyl(lower)alkenyl, halogen, nitro, cyano, —$OR^6$ (in which $R^6$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkylbenzenesulfonyl) and —$CH_2$—Z'—$R^7$ (in which Z' is —O—, —S—, —SO— or —NR— (R being hydrogen or lower alkyl) and $R^7$ is phenyl, halophenyl, lower alkoxyphenyl, pyridyl or pyrimidinyl).

A main object of the present invention is to provide the alkoxyiminoacetamides of the formula (I) as novel chemical substances. Another object of this invention is to provide the alkoxyiminoacetamides (I) useful as fungicides, particularly as an agricultural fungicide. A further object of the invention is provide a fungicidal compostiion comprising at least one of the alkoxyiminoacetamides (I) as the active ingredient. A still further object of the invention is to provide a process for preparing the alkoxyiminoacetamides (I). These and other objects of the invention will be apparent to those skilled in the art from the foregoing and subsequent descriptions.

Within the formula (I), there are included the alkoxyiminoacetamides of the following formulas:

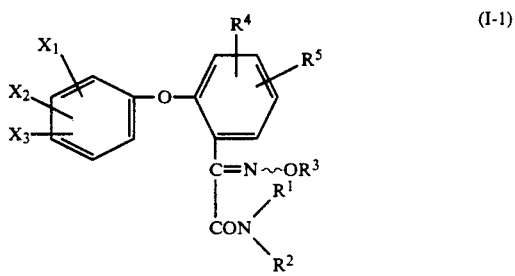
(I-1)

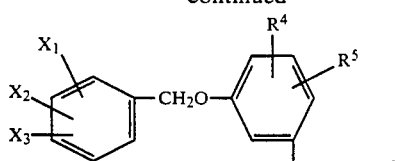
(I-2)

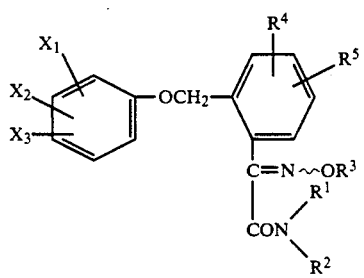
(I-3)

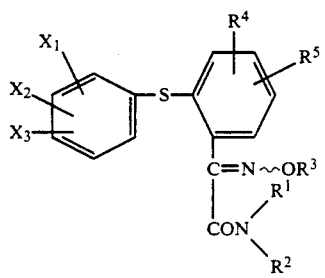
(I-4)

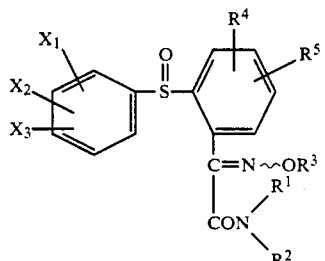
(I-5)

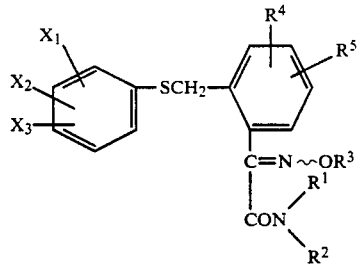
(I-6)

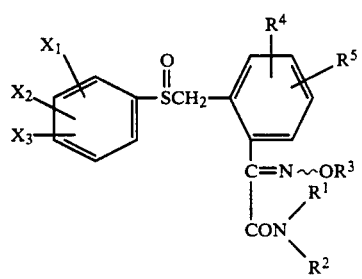
(I-7)

wherein $R^1$ and $R^2$ are each hydrogen or lower alkyl (particularly methyl), $R^3$ is lower alkyl (particularly methyl), $R^4$ and $R^5$ are each hydrogen, lower alkyl (particularly methyl), lower alkoxy (particularly methoxy), halogen-substituted lower alkyl (particularly trifluoromethyl), lower alkyl-substituted silyl (particularly trimethylsilyl), halogen (particularly, chlorine, iodine or fluorine) or nitro and $X_1$, $X_2$ and $X_3$ are each hydrogen, lower alkyl (particularly methyl, ethyl, propyl, isopropyl, butyl or t-butyl), lower alkoxy (particularly methoxy), lower alkanoyl (particularly acetyl), halogen-substituted lower alkyl (particularly trifluoromethyl), lower alkyl-substituted silyl (particularly trimethylsilyl), halogen (particularly chlorine, bromine or fluorine), nitro, di(lower)alkylamino (particularly dimethylamino), phenyl, phenyl(lower)alkenyl, (particularly phenylethenyl), furyl(lower)alkenyl (particularly furylethenyl), hydroxyl, lower alkynyloxy (particularly 2-propynyloxy), lower alkanoyloxy (particularly acetoxy), benzoyloxy, phenoxy, lower alkoxyphenoxy (particularly methoxyphenoxy), nitrophenoxy, benzyloxy, cyanobenzyloxy, tetrahydropyranyloxy, pyrimidinyloxy, pyridyloxy, trifluoromethylpyridyloxy, benzothiazolyloxy, quinalyoxy, benzoyl(lower)alkoxy (particularly benzoylmethoxy), benzenesulfonyloxy or lower alkylbenzenesulfonyloxy (particularly toluenesulfonyloxy).

In addition to the above alkoxyiminoacetamides (I), there are also included the following ones:

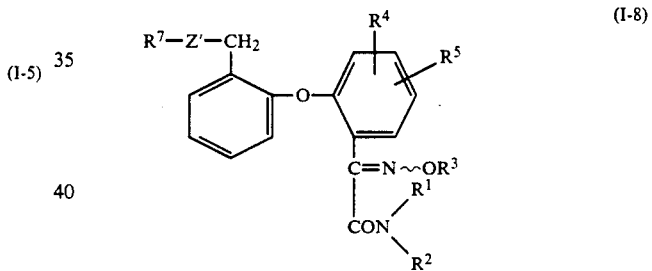
(I-8)

wherein $R^1$ and $R^2$ are each hydrogen or lower alkyl (particularly methyl), $R^3$ is lower alkyl (particularly methyl), $R^4$ and $R^5$ are each hydrogen, lower alkyl (particularly methyl), lower alkoxy (particularly methoxy), halogen-substituted lower alkyl (particularly trifluoromethyl), lower alkyl-substituted silyl (particularly trimethylsilyl), halogen (particularly, chlorine, iodine or fluorine) or nitro, Z' is —O—, —S—, —SO— or —NR— (in which R is lower alkyl, particularly methyl), $R^7$ is phenyl, lower alkoxyphenyl (particularly methoxyphenyl, halophenyl (particularly bromophenyl), pyridyl or pyrimidinyl;

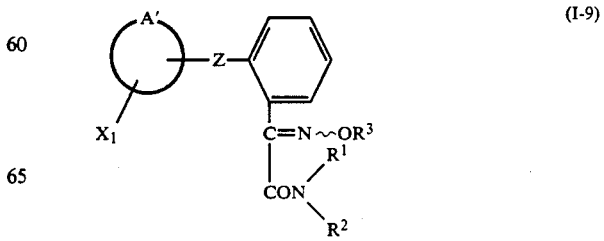
(I-9)

wherein $R^1$ and $R^2$ are each hydrogen or lower alkyl (particularly methyl), $R^3$ is lower alkyl (particularly methyl),

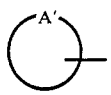

A is pyridyl or pyrimidinyl, Z is —O—, —OCH$_2$— or —CH$_2$O— and $X_1$ is hydrogen or trifluoromethyl;

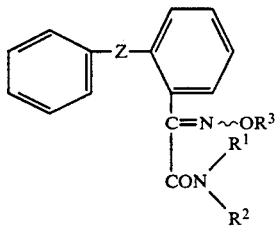
(I-10)

wherein $R^1$ and $R^2$ are each hydrogen or lower alkyl (particularly methyl), $R^3$ is lower alkyl (particularly methyl) and Z is —CH$_2$CH$_2$—,

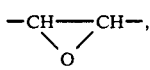

—CH=CH—, —CH(OH)— or —CO—; and

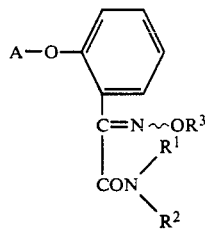
(I-11)

wherein $R^1$ and $R^2$ are each hydrogen or lower alkyl (particularly methyl), $R^3$ is lower alkyl (particularly methyl) and A is alkenyl of 3 to 10 carbon atoms optionally substituted with not more than 3 halogen atoms (particularly chlorine) or alkadienyl of 3 to 10 carbon atoms optionally substituted with not more than 3 halogen atoms (particularly chlorine).

The alkoxyiminoacetamides (I) may be produced by various processes, among which a typical standard process starts from the corresponding oxocarboxylic acid of the formula:

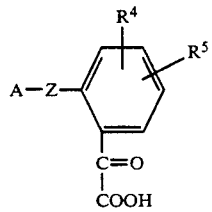
(II)

wherein A and Z are each as defined above and substantially comprises amidation and alkoximation (alkoxime-formation), or vice versa. Namely, the core portion of such process is represented by Scheme A:

Scheme A

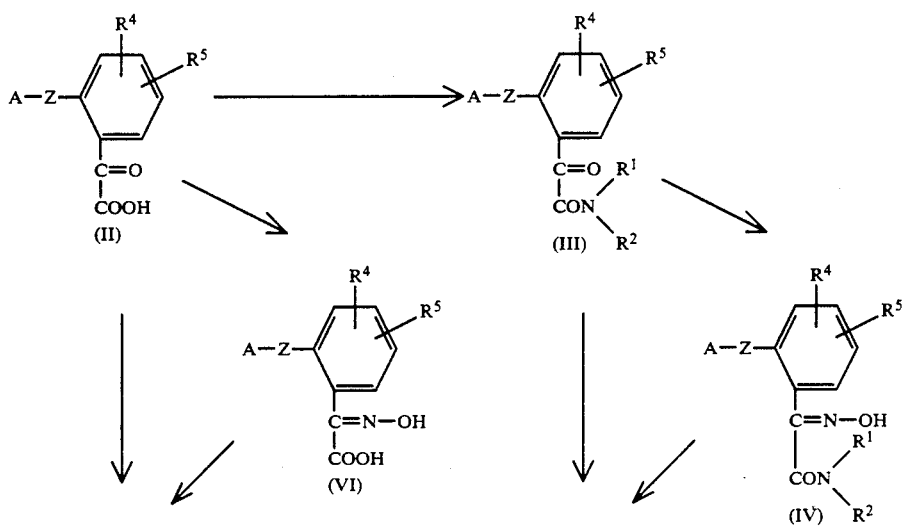

-continued
Scheme A

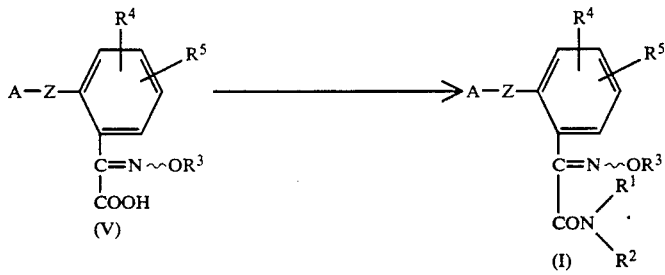

wherein $R^1$, $R^2$, $R^3$, $R^4$, $R^5$, A and Z are each as defined above.

Explaining the conversions in Scheme A, the oxocarboxylic acid (II) or its derivative on the carboxyl group is reacted with an amine of the formula:

wherein $R^1$ and $R^2$ are each as defined above (amidation), and the resultant oxocarbonamide (III) is reacted with an alkoxyamine of the formula:

wherein $R^3$ is as defined above (alkoximation) to give the objective alkoxyiminoacetamide (I).

When $R^1$ in the amine (a) is hydrogen, the reaction proceeds not only on the carboxyl group but also on the carbonyl group in the oxocarboxylic acid (II) or its derivative on the carboxyl group so that the following iminocarbonamide is by-produced:

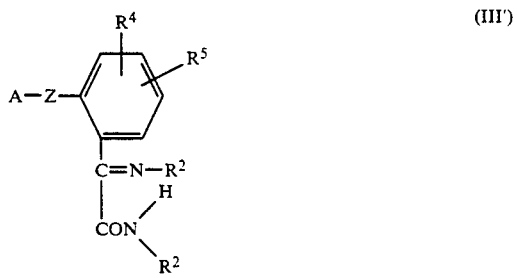

wherein $R^2$, $R^4$, $R^5$, A and Z are each as defined above. Particularly when such amine (a) is used in two moles or more to one mole of the oxocarboxylic acid (II) or its derivative, the iminocarbonamide (III') is obtainable as a main product. Not only the oxocarbonamide (III) but also the iminocarbonamide (III') can be converted into the objective alkoxyiminoacetamide (I), when reacted with the alkoxyamine (b).

When desired, the alkoximation may be effected in two steps, i.e. reaction of the oxocarbonamide (III) or the iminocarbonamide (III') with hydroxylamine and reaction of the resultant hydroxyiminoacetamide (IV) with an alkylating agent of the formula:

wherein X is an acid residue such as a halogen atom (e.g. chlorine, bromine) or a sulfonyl group (e.g. methanesulfonyloxy, ethanesulfonyloxy, toluenesulfonyloxy).

Alternatively, the oxocarboxylic acid (II) or its derivative on the carboxyl group is reacted with the alkoxyamine (b) (alkoximation), and then the resulting alkoxyiminocarboxylic acid (V) or its derivative on the carboxyl group is reacted with the amine (a) (amidation) to give the objective alkoxyiminoacetamide (I).

When desired, the alkoximation may be effected in two steps, i.e. reaction of the oxocarboxylic acid (II) or its derivative on the carboxyl group with hydroxylamine and reaction of the resulting hydroxyiminocarboxylic acid (VI) or its derivative on the carboxyl group with the alkylating agent (c).

The thus produced alkoxyiminocarboxylic acid (V) or its derivative on the carboxyl group is then reacted with the amine (a) to give the objective alkoxyiminoacetamide (I).

As understood from the above, the oxocarboxylic acid (II) as the starting material in the above process may be used as the free acid or its derivative. Examples of the derivative are acid esters, acid anhydrides, acid halides, etc.

Any reaction included in the above process such as the amidation (reaction with the amine (a)), the alkoximation (reaction with the alkoxyamine (b)), the oximation (reaction with hydroxylamine) and the alkylation (reaction with the alkylating agent (c)) is per se conventional and may be carried out in a manner as commonly known to those skilled in the art. In general, those reactions are performed in a solvent, preferably under the condition to facilitate or promote their proceeding at a temperature of room temperature to the reflux temperature of the reaction mixture, e.g. from 10° to 200° C.

The condition to facilitate or promote the proceeding of the reaction may be appropriately taking into consideration the kinds of the reactants or the kinds of the by-products to be eliminated from the reactants. For instance, the amidation proceeds between a carboxylic acid or its derivative on the carboxyl group such as an acid ester (e.g. methyl ester, ethyl ester, cyanomethyl ester, p-nitrophenyl ester), an acid anhydride (e.g. a mixed acid anhydride with trichloroacetic acid) or an acid halide (e.g. acid chloride, acid bromide) and the amine (a) to give a carbonamide by-producing water, an alcohol, an acid or the like. In order to eliminate these by-products, a condensing agent (e.g. 1,3-dicyclohexylcarbodiimide, N-cyclohexyl-N'-morpholinoethylcarbodiimide, 1,3-diisopropylcarbodiimide, methyl chlorocarbonate, ethyl chlorocarbonate), a dehydrating agent (e.g. thionyl chloride, sulfuryl chloride, phosphorus oxychloride, phosphorus tribromide, phosphorus pentachloride, polyphosphoric acid), an acid-eliminating agent (e.g. pyridine, triethylamine, sodium methoxide, sodium hydroxide, sodium carbonate), etc. may be used. Further, for instance, the alkoximation proceeds between a ketone and the alkoxyamine (b) to give an alkoxime by-producing water. Usually, a base such as sodium hydroxide, sodium acetate or pyridine is incorporated into the reaction system.

The reaction is normally effected in an inert solvent appropriately chosen depending upon the kind of the reaction from dioxane, methylene chloride, chloroform, diethyl ether, tetrahydrofuran, acetone, dimethylformamide, dimethylsulfoxide, pyridine, acetonitrile, benzene, toluene, xylene, etc.

As stated above, Scheme A shows only the core portion of the typical standard process, and it is of course possible to produce the oxocarbonamide (III) or the alkoxy-iminocarboxylic acid (V) by any other process not going through the oxocarboxylic acid (II) in a conventional manner. Also, the once produced alkoxyiminoacetamide (I) may be subjected to conversion on any substituent on the benzene ring such as represented by $R^4$, $R^5$ or —Z—A.

Referring to Scheme 1 to 11 as hereinafter given, some specific procedures for production of the alkoxyiminoacetamides (I) will be explained in details. In Scheme 1 to 11, Me is methyl, Hal is halogen, X is an acid residue such as halogen, Z" is —O—, —S— or —NR— (R being lower alkyl) and $R^4$, $R^5$, $R^6$, $R^7$, $X_1$, $X_2$ and $X_3$ are each as defined above.

Scheme 1:

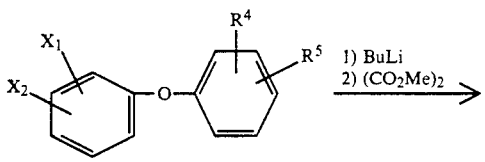

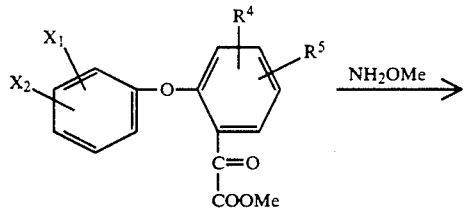

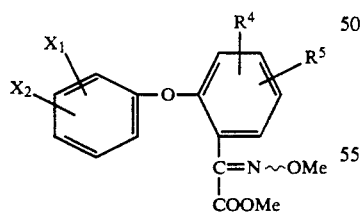

Scheme 2:

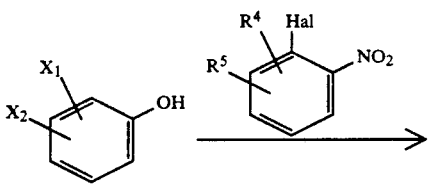

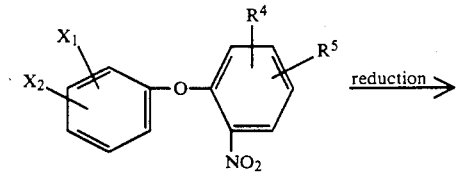

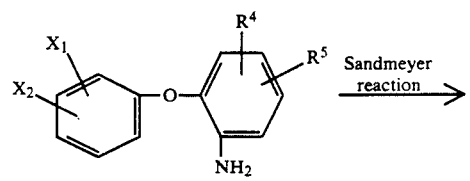

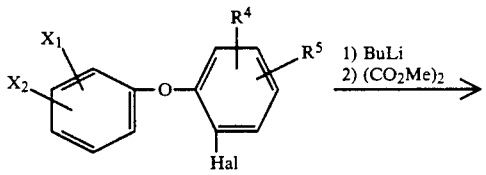

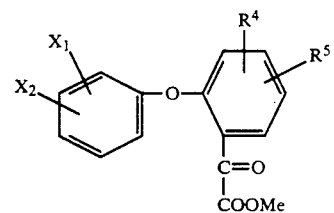

Scheme 3:

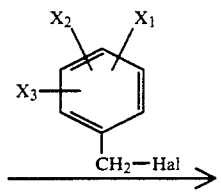

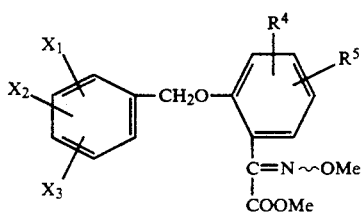

Scheme 4:

Scheme 5:
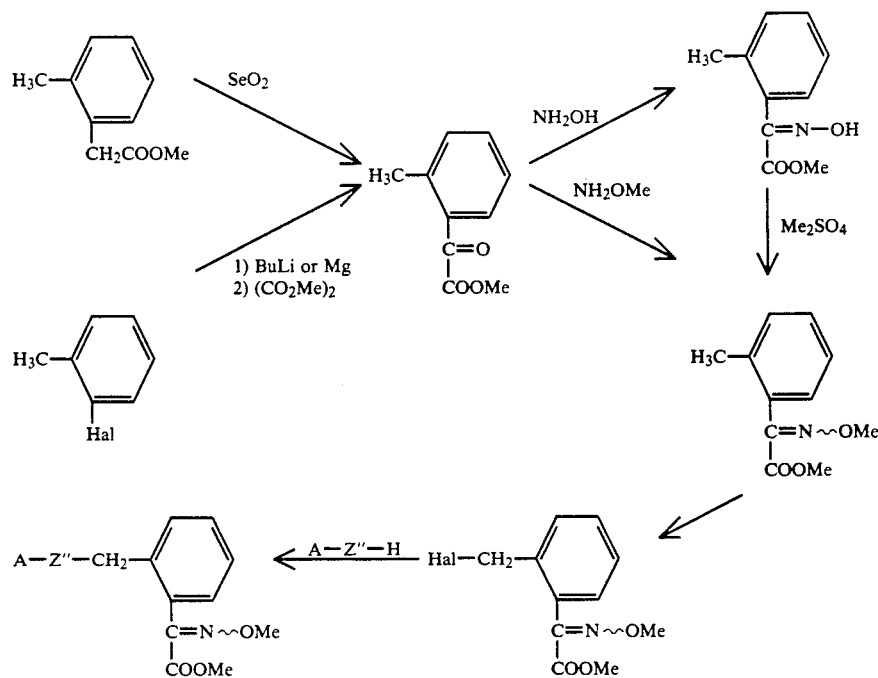
-continued
Scheme 6
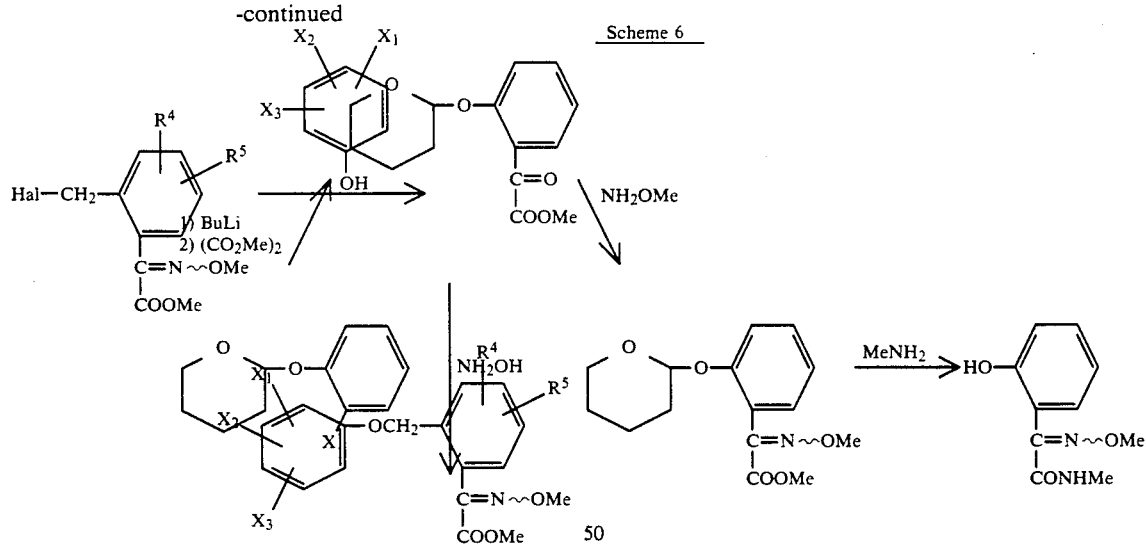

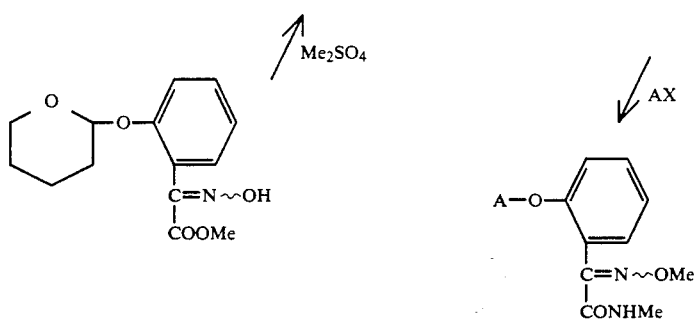
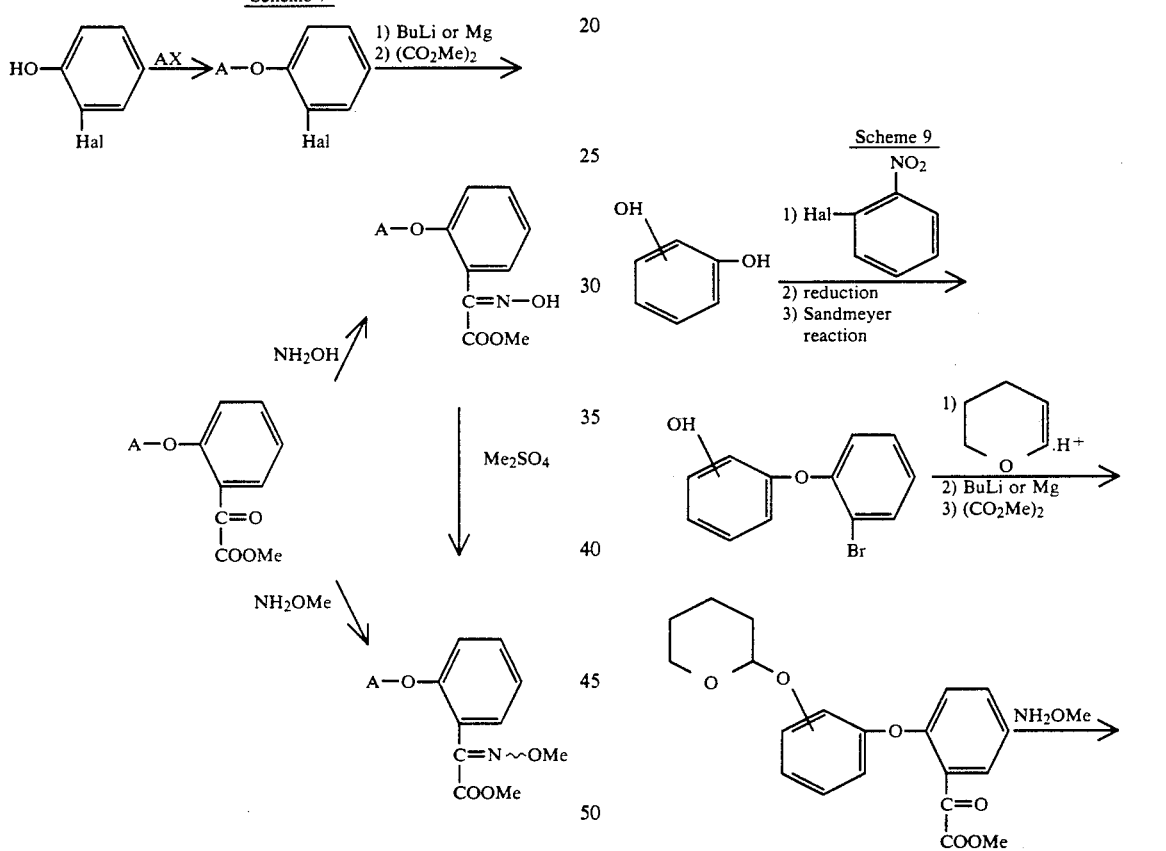
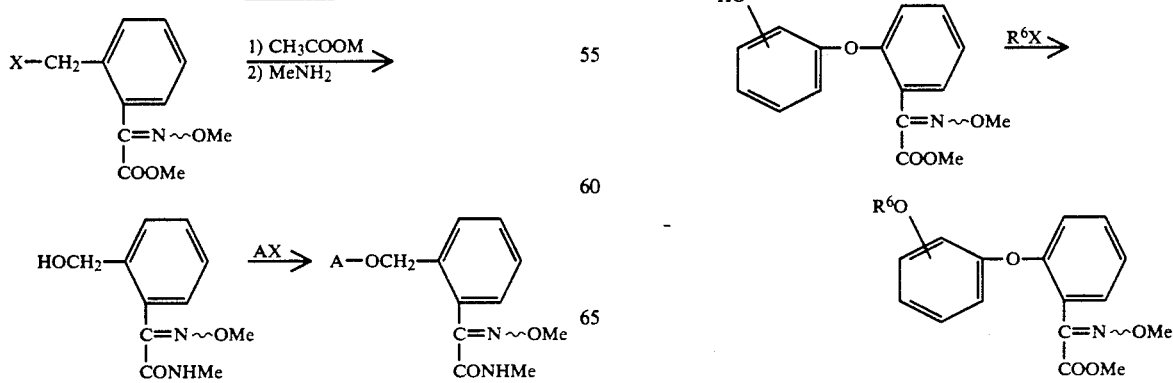

Scheme 10

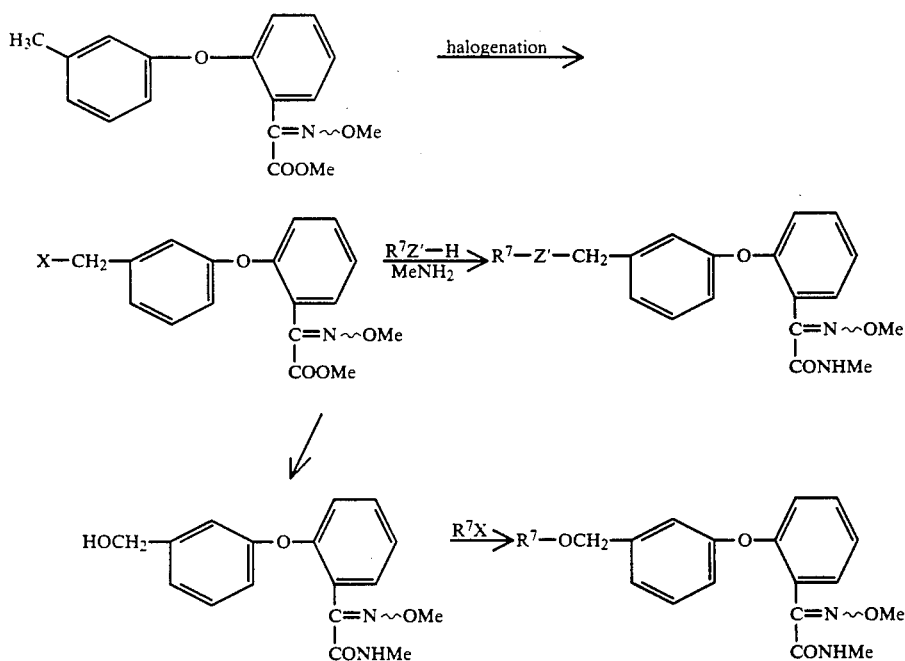

Scheme 11

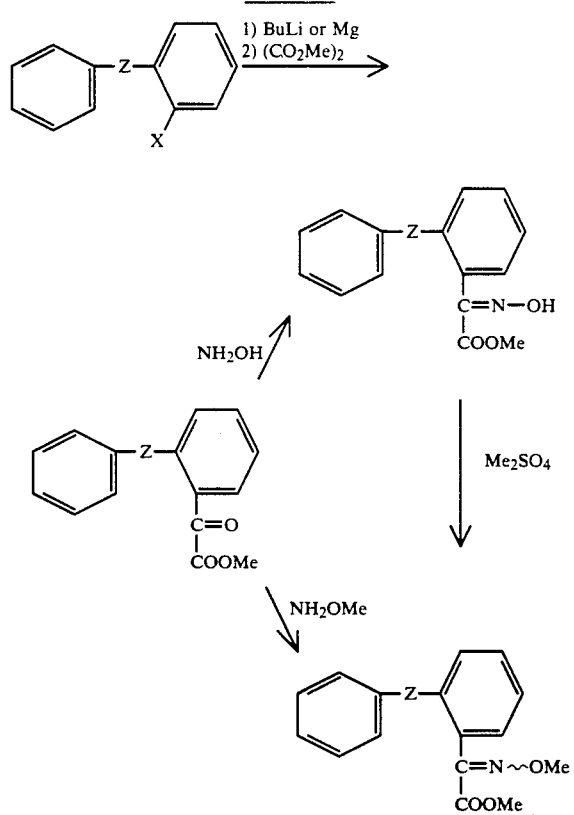

In Scheme 1, the starting diphenyl ether is reacted with butyl lithium to introduce lithium into the 2 position on the benzene ring, followed by reaction with dimethyl oxalate to give a ketonic ester as an example of the derivative of the oxocarboxylic acid (II). Then, the ketonic ester is reacted with methoxyamine to give a methoxyiminoacetic acid ester, which is an example of the derivative of the alkoxyiminocarboxylic acid (V).

In Scheme 2, the starting phenol is reacted with a nitrophenyl halide in the presence of a base (e.g. sodium amide, potassium carbonate) in an inert solvent (e.g. dimethylsulfoxide, dimethylformamide) to give a diphenyl ether. The diphenyl ether is subjected to reduction on the nitro group, and the resultant amine is subjected to Sandmeyer's reaction for conversion of the amino group into a halogen atom. Then, the halogenated compound is reacted with butyl lithium, followed by condensation with dimethyl oxalate to a ketonic ester. This ketonic ester is an example of the derivative of the oxocarboxylic acid (II).

In Scheme 3, the starting phenol is reacted with a benzyl halide in the presence of a base (e.g. sodium amide, triethylamine, sodium hydroxyde, barium oxide, silver oxide, sodium hydride) in an inert solvent (e.g. ether, dimethylsulfoxide, dimethylformamide, tetrahydrofuran) to give a benzyl phenyl ether, which is an example of the derivative of the alkoxyiminocarboxylic acid (V).

In Scheme 4, the starting benzyl halide, obtained from the corresponding tolyl compound by the reaction with a halogenating agent (e.g. chlorine, bromine, t-butyl hypohalogenite, N-halosuccinimide, trichloromethanesulfonyl halide) at a high temperature or in the presence of light or a peroxide, is reacted with a phenol in the same manner as in Scheme 3 to give a phenyl benzyl ether as an example of the derivative of the alkoxyiminocarboxylic acid (V).

In Scheme 5, methyl 2-tolylacetate is oxidized with selenium oxide, or 2-tolyl halide is reacted with butyl lithium or magnesium, followed by reaction with dimethyl oxalate, whereby a ketonic ester is obtained. The ketonic ester is reacted with methoxyamine hydrochloride to give a methoxime. Alternatively, the ketonic ester is first reacted with hydroxylamine hydrochloride, and then the resultant oxime is reacted with dimethyl sulfate in the presence of a base to give a methoxime. The thus produced methoxime is subjected to halogenation so that the methyl group on the benzene ring is converted into a halomethyl group. The resultant benzyl halide is then reacted with a reagent of the formula: A—ZΔ—H (wherein Z" is —O—, —S— or —NR— (R being lower alkyl)) in a reactive form in the presence of a base to give a methoxyiminoacetic acid ester, which is an example of the derivative of the alkoxyiminocarboxylic acid (V).

In Scheme 6, the starting tetrahydropyranyloxyphenyl halide is reacted with butyl lithium, followed by reaction with dimethyl oxalate to give a ketonic ester. The ketonic ester is then reacted with methoxyamine hydrochloride or with hydroxylamine hydrochloride and dimethyl sulfate in order to give a tetrahydropyranyl phenyl ether, which is an example of the derivative of the alkoxyiminocarboxylic acid (V). The tetrahydropyranyl phenyl ether is then treated with methylamine, whereby the carboxylic ester is converted into a carbonamide simultaneously with elimination of the tetrahydropyranyl group. The resultant phenol is reacted with an alkenyl or alkadienyl halide in the presence of a base to give an alkenyl or alkadienyl phenyl ether, which is an example of the alkoxyiminoacetamide (I).

In Scheme 7, the starting hydroxyphenyl halide is reacted with an aryl halide (e.g. phenyl bromide, pyridyl bromide) to give an aryloxyphenyl halide. The aryloxyphenyl halide is converted into an aryl phenyl ether in the same manner as in Scheme 6, i.e. by reaction with butyl lithium or magnesium, followed by treatment with dimethyl oxalate and reaction with methoxyamine hydrochloride or with hydroxylamine hydrochloride and then dimethyl sulfate. The aryl phenyl ether is an example of the derivative of the alkoxyiminocarboxylic acid (V).

In Scheme 8, the starting iminoacetic acid ester is reacted with methylamine and an alkali metal acetate, whereby the ester group is converted into a carbonamide group and the halomethyl group is converted into a hydroxymethyl group. The resultant hydroxyphenylcarbonamide is reacted with an aryl halide (e.g. phenyl halide, pyrimidinyl halide) in the presence of a base to give an aryl benzyl ether, which is an example of the alkoxyiminoacetamide (I).

In Scheme 9, the starting dihydroxybenzene is reacted with 2-halonitrobenzene in the presence of a base, and the resultant nitrodiphenyl ether is subjected to reduction and Sandmeyer reaction in order to give 2-(hydroxyphenoxy)phenyl halide, which is then reacted with dihydropyrane in the presence of an acid catalyst (e.g. sulfuric acid, hydrochloric acid, boron trifluoride). The resultant tetrahydropyranyloxyphenyloxyphenyl halide is reacted with butyl lithium or magnesium and then with dimethyl oxalate to give a ketonic ester as an example of the derivative of the oxocarboxylic acid (II). This ketonic ester is reacted with methoxyamine hydrochloride to give a methoxime as an example of the derivative of the alkoxyiminocarboxylic acid (V). Thereafter, the methoxime is reacted with $R^6X$ (wherein $R^6$ and X are each as defined above) (e.g. phenyl halide, pyridyl halide, pyrimidinyl halide, quinolyl halide, benzothiazolyl halide, phenacyl halide, tosyl halide, acetyl halide, benzoyl halide, benzyl halide, propargyl halide, styryl halide) so as to convert the hydroxyl group into an $R^6O$— group.

In Scheme 10, the starting methoxime is halogenated to give the corresponding halomethyl compound, which is then treated with an alkali metal acetate and methylamine to give a methoxyiminocarbonamide as an example of the alkoxyiminoacetamide (I). This methoxyiminocarbonamide is reacted with a group-introducing reagent of the formula: $R^7X$ in the presence of a base, whereby the hydroxyl group is converted into —$OR^7$. Alternatively, said halomethyl compound is reacted with a reagent of the formula: $R^7$—Z'—H (wherein $R^7$ and Z' are each as defined above) and methylamine to give a methoxyiminocarbonamide as another example of the alkoxyiminoacetamide (I).

In Scheme 11, the starting phenyl halide is reacted with butyl lithium or magnesium and then with dimethyl oxalate to give a ketonic ester as an example of the derivative of the oxocarboxylic acid (II). The ketonic ester is reacted with methoxyamine hydrochloride or with hydroxylamine and dimethyl sulfate in order to give a methoxime as an example of the derivative of the alkoxyiminocarboxylic acid (V).

The alkoxyiminoacetamides (I) thus produced are usually obtained as a mixture of the E and Z forms, which can be separated into each of those forms.

The alkoxyiminoacetamides (I) show a strong fungicidal activity against a wide variety of phytopathogenic fungi on crop plants (e.g. rice plant, wheat, berly, rye, corn, common millet, millet, buck wheat, soybean, redbean, peanut), vegetables (e.g. cucumber, eggplant, tomato, pumpkin, kidney bean), fruit trees (e.g. citrus fruits, grape, apple, pear, peach), etc. They also show a fungicidal activity against phytopathogenic fungi in soil. Examples of the phytopathogenic fungi on which the alkoxyiminoacetamides (I) exert their fungicidal activity are *Pyricularia oryzae, Rhizoctonia solani, Erysiphe graminis, Sphaerotheca fuliginea, Erysiphe cichoracearum, Phytophthora infestans, Pseudoperonospora cubensis, Peronospora manshurica, Plasmopara viticola, Botrytis cinerea, Pythium aphanidermatium, Sclerotinia sclerotiorum, Corticium rolfsii*, etc. Therefore, the alkoxyiminoacetamides (I) are useful as agricultural fungicides.

Application of the alkoxyiminoacetamides (I) may be performed before and/or after the infection with phytopathogenic fungi on plants. Application may be made to plants by any conventional procedure such as atomizing, scattering or spreading. Application may be also made through treatment of seeds of plants, soil where plants grow, paddy field for seedling or water for perfusion with the alkoxyiminoacetamides (I).

For the practical usage, the alkoxyiminoacetamides (I) may be applied as such or in a formulation form such as solutions, emulsions, dispersions, dusts, wettable powders, oil sprays, emulsifiable concentrates, tablets, granules, fine granules, aerosols or flowables. Such formulation form can be prepared in a conventional manner by mixing at least one of the alkoxyiminoacetamides (I) with an appropriate solid or liquid carrier(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon), chemical fertilizers (e.g. ammonium sulfate, ammonium phosphate, ammonium nitrate, urea, ammonium chloride), etc.

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichlorocarbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents or dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

In addition to the above components, other fungicides, insecticides, herbicides, fertilizers, etc. may be incorporated into the composition.

The composition as above formulated generally contains at least one of the alkoxyiminoacetamides (I) in a concentration of about 1 to 95% by weight, preferably of about 2.0 to 80% by weight. By using such composition as such or in a diluted form, the alkoxyiminoacetamides (I) are generally applied in such amounts as about 1.0 g to 5 kg/hectare, preferably about 2 to 100 g/hectare, usually in contrations ranging from about 1 to 50,000 ppm, preferably from about 100 to 5,000 ppm.

Practical and presently preferred embodiments of the invention are illustratively shown in the following examples wherein the abbreviations indicate the following meanings: Me, methyl; OMe, methoxy; SiMe$_3$, trimethylsilyl; Me$_2$N, dimethylamino; (i)Pr, isopropyl; (i)PrO, isopropoxy; Ph, phenyl; OPh, phenoxy; tBu, t-butyl.

EXAMPLE 1

Production of 2-(2-phenoxyphenyl)-2-methoxyiminoacetamide (Compound No. 1)

To a solution of methyl-(2-phenoxyphenyl)-2-oxoacetate (0.70 g) in methanol (10 ml), 28% aqueous ammonium hydroxide (2.0 ml) was added, and the resultant mixture was stirred overnight, followed by removal of the solvent under reduced pressure. The residue was combined with diethyl ether (150 ml) and water (50 ml) under stirring and, upon dissolution, allowed to stand. The organic layer was separated, washed and dried over anhydrous sodium sulfate. Upon filtration, the filtrate was concentrated under reduced pressure to give residual yellow crystals, which were combined with methanol (10 ml) and O-methylhydroxylamine hydrochloride (1.49 g) while stirring and refluxed for 6 hours. Water (50 ml) was added to the reaction mixture, which was extracted with diethyl ether. The organic layer was washed with water and dried over anhydrous sodium sulfate, followed by filtration. The filtrate was concentrated under reduced pressure to give oily residue. The residue was purified by silica gel column chromatography with benzene to give 0.36 g of the objective compound. $n_D^{23.3}$ 1.5978.

Elementary analysis (%) for $C_{15}H_{14}H_2O_3\cdot\frac{1}{2}H_2O$:
Calcd.: C, 64.50; H, 5.41; N, 10.03.
Found: C, 64.63; H, 5.13; N, 9.89.

EXAMPLE 2

Production of N-methyl-2-(2-phenoxyphenyl)-2-methoxyiminoacetamide (isomeric mixture of Compound No. 3 and Compound No. 4)

To a solution of methyl-2-phenoxyphenyl-2-oxoacetate (0.70 g) in methanol (10 ml), 5% aqueous methylamine (3.4 ml) was added, and the resultant mixture was stirred overnight, followed by removal of the solvent under reduced pressure. The residue was combined with diethyl ether (150 ml) and water (50 ml) under stirring and, upon dissolution, allowed to stand. The organic layer was separated, washed and dried over anhydrous sodium sulfate. Upon filtration, the filtrate was concentrated under reduced pressure to give an oily residue, which was purified by silica gel column chromatography with a mixture of benzene and ethyl acetate (100 : 5). High polar eluate was concentrated under reduced pressure to give an oily residue (0.55 g), which was combined with methanol (10 ml) and 0-methyl hydroxylamine hydrochloride (0.40 g) under stirring and refluxed for 7 hours. Water (50 ml) was added to the reaction mixture, wich was extracted with diethyl ether (150 ml). The extract was washed with water, dried and concentrated under reduced pressure. The residue was purified by silica gel column chromatography with a mixture of benzene and ethyl acetate (100:5), whereby 0.25 g of Compound No. 3 was obtained as white crystals (m.p., 63°-64.5° C.) from the first eluate and 0.15 g of Compound No. 4 was obtained as white crystals (m.p., 48°-51° C.) from the second eluate.

Elementary analysis (%) for $C_{16}H_{16}N_2O_3\cdot1/5H_2O$:
Compound No. 3:
Calcd.: C, 66.74; H, 5.74; N, 9.73.
Found: C, 66.75; H, 5.68; N, 9.71.
Compound No. 4:
Calcd.: C, 66.74; H, 5.74; N, 9.73.
Found: C, 66.85; H, 5.90; N, 9.66.

EXAMPLE 3

Production of N,N-dimethyl-2-(2-phenoxyphenyl)-2-methoxyiminoacetamide (Compound No. 2)

To a solution of methyl-2-(2-phenoxyphenyl)-2-oxoacetic acid (0.70 g) in methanol (10 ml), 50% aqueous dimethylamine (2.5 ml) was added, and the resultant mixture was stirred overnight. The reaction mixture was treated in the same manner as in Example 1 to give an oily residue (0.50 g). The residue was combined with methahol (10 ml) and O-methylhydroxylamine hydrochloride (0.34 g), followed by stirring for 7 hours. The reaction mixture was treated in the same manner as in Example 2 to give 0.26 g of the objective compound as white crystals. m.p., 63°-64° C.

Elementary analysis (%) for $C_{17}H_{18}N_2O_3$:
Calcd.: C, 68.44: H, 6.08; N, 9.38.
Found: C, 68.44; H, 6.21; N, 9.48.

EXAMPLE 4

Production of N-methyl-2-(2-phenoxyphenyl)-2-methoxyiminoacetamide (Compound No. 3)

A solution of N-methyl-2-(2-phenoxyphenyl)-2-oxoacetamide (1.50 g) and hydroxylamine hydrochloride (0.69 g) in methanol (10 ml) was refluxed for 220 minutes while stirring, and water (75 ml) was added to the reaction mixture, followed by extraction with dichloromethane twice (150 ml and 100 ml). The organic layer was washed with water (75 ml) and dried over anhydrous sodium sulfate. Upon filtration, the filtrate was concentrated under reduced pressure to give a crystalline residue. The residue was combined with dimethylformamide (DMF) (7 ml), potassium carbonate (1.6 g) and dimethyl sulfate (0.58 ml) and stirred overnight. The reaction mixture was treated in the same manner as in Example 2 to give 0.80 g of the objective compound as an isomeric product.

EXAMPLE 5

Production of (Z)-N-methyl-2-[2-(3-tolyloxy)-phenyl]-2-methoxyiminoacetamide (Compound No. 5)

(1) To a solution of 3-phenoxytoluene (2.00 g) in diethyl ether (30 ml), a solution of butyl lithium in hexane (14.1 mmol) was added at 0° C., followed by stirring at room temperature for 12 hours. A solution of dimethyl oxalate (2.57 g) in diethyl ether (30 ml) was dropwise added thereto at 0° C., and the resultant mixture was stirred for 5 hours and neutralized with 1 hydrochloric acid, followed by extraction with diethyl ether. The solvent was dried and evaporated, and the residue was purified by silica gel column chromatography with a mixture of hexane and ethyl acetate to give a mixture of the following products, of which "$^1$H-NMR" was measured in chloroform-$d_1$ (CDCl$_3$) with 270 MHz spectrometer and chemical shifts are reported in ppm down field from tetramethylsilane as an internal standard. The coupling constant (J) is to be represented by Hz. Abbreviations specifically denotes the following meanings: s, singlet; d, doublet; t, triplet; q, quartet; sept, septet; brs, broad singlet; brd, broad doublet; m, multiplet.

Product (A):
Methyl-2-[2-(3-tolyloxy)phenyl]-2-oxoacetate (yield, 965 mg)

$^1$H-NMR: 2.35 (3H, s), 3.72 (3H, s), 6.86 (1H, d, J =7.8), 6.88 (1H, s), 7.00 (1H, d, J =7.8), 7.17–7.28 (3H, m), 7.51 (1H, td, J =7.8, 2.0), 7.96 (1H, dd, J =7.8, 2.0);

Product (B):
Methyl-2-(4-methyl-2-phenoxyphenyl)-2-(4-methyl-2-phenoxyphenyl)-2-oxoacetate (yield, 260 mg)

$^1$H-NMR: 2.32 (3H, s), 3.69 (3H, s), 6.65 (1H, s), 7.03–7.11 (2H, m), 7.14–7.19 (2H, m), 7.34–7.38 (2H, m), 7.88 (1H, d, J =7.8).

(2) Product (A) (965 mg), i.e. methyl-2-[2-(3-tolyloxy)phenyl]-2-oxoacetate as obtained (1) above, and O-methylhydroxylamine hydrochloride (597 mg) were dissolved in methanol (2 ml), and the resultant mixture was heated under reflux for 5 hours. The reaction mixture was cooled to room temperature, followed by removal of ethanol. The residue was added to water and extracted with diethyl ether. The solvent was dried and evaporated to give a mixture of the following products:

Product (A'):
Methyl-(Z)-2-[2-(3-tolyloxy)phenyl]-2-methoxyiminoacetate (yield, 286 mg)

$^1$H-NMR: 2.32 (3H, s), 3.65 (3H, s), 4.02 (3H, s), 6.75–6.94 (3H, m), 7.12–7.36 (4H, m), 7.83 (1H, d, J =7.8);

Product (B'):
Methyl-(E)-2-(3-tolyloxy)phenyl]-2-methoxyiminoacetate (739 mg)

$^1$H-NMR: 2.32 (3H, s), 3.78 (3H, s), 4.03 (3H, s), 6.77–6.92 (3H, m), 7.11–7.38 (5H, m).

(3) To Product (A') (286 mg), i.e. methyl-(Z)-2-[2-(3-tolyloxy)phenyl]-2-methoxyiminoacetate, [2-(3-tolyloxy)phenyl]-2-methoxyiminoacetate, 30 % methanolic methylamine (197 mg) was added, followed by stirring at room temperature for 12 hours. Excess amine and methanol were removed from the mixture, which was subjected to silica gel column chromatography with a mixture of hexane and ethyl acetate to give 201 mg of (Z)-N-methyl-2-[2-(3-tolyloxy)phenyl]-2-methoxyiminoacetamide (Compound No. 5).

EXAMPLE 6

Production of (E)-N-methyl-2-[2-(3-tollyloxy)phenyl]-2-methoxyiminoacetamide (Compound No. 6)

In the same manner as in Example 5, the objective compound was prepared from methyl-(E)-2-[2-(3-tollyloxy)phenyl]-2-methoxyiminoacetate (Product (B)).

EXAMPLE 7

Production of (Z)-N-methyl-2-(4-methyl-2-phenoxyphenyl)-2-methoxyiminoacetamide (Compound No. 7)

In the same manner as in Example 5, the objective compound was prepared from methyl-(Z)-2-(4-methyl-2-phenoxyphenyl)-2-methoxyiminoacetate (Product (B)).

EXAMPLE 8

Production of (E)-N-methyl-2-(4-methyl-2-phenoxyphenyl)-2-methoxyiminoacetamide (Compound No. 8):

In the same manner as in Example 5, the objective compound was prepared from methyl-(E)-2-(4-methyl-2-phenoxyphenyl)-2-methoxyiminoacetate. cl EXAMPLE 9

Production of (E)-N-methyl-2-(6-methoxy-2-phenoxyphenyl)-2-methoxyiminoacetamide (Compound No. 9)

In the same manner as in Example 5, the objective compound was prepared from 3-methoxydiphenyl ether.

EXAMPLE 10

Production of (E)-N-methyl-2-(5-nitro-2-phenoxyphenyl)-2-methoxyiminoacetamide (Compound No. 10)

(E)-N-Methyl-2-(2-phenoxyphenyl)-2-methoxyiminoacetamide (500 mg) was dissolved in acetic anhydride (1 ml), and the resultant mixture was cooled to 0° C. Fuming nitric acid (302 mg) was added thereto, and the mixture was stirred at the same temperature for 30 minutes. Excess methanolic ethylamine was added thereto, followed by stirring for 12 hours. The reaction mixture was diluted with water and extracted with diethyl ether. The solvent was dried and the residue was subjected to high performance liquid chromatography (HPLC) to give 86 mg of the objective compound.

In the same manner as above, there were obtained the following compounds:
(E)-N-methyl-2-[2-(4-nitrophenoxy)phenyl]-2-methoxyiminoacetamide (Compound No. 11; 167 mg);
(E)-N-methyl-2-[2-(2-nitrophenoxy)phenyl]-2-methoxyiminoacetamide (Compound No. 12; 45 mg);
(E)-N-methyl-2-(3-nitro-2-phenoxyphenyl)-2-methoxyiminoacetamide (Compound No. 13; 43 mg).

EXAMPLE 11

Production of
(E)-N-methyl-2-[2-(4-chlorophenoxy)-phenyl]-2-methoxyiminoacetamide (Compound No. 16)

A solution of (E)-N-methyl-2-(2-phenoxyphenyl)-2-methoxyiminoacetamide (500 mg) in dichloromethane was cooled to 0° C., and sulfuryl chloride (285 mg) was dropwise added thereto. The resultant mixture was stirred at the same temperature for 2 hours, diluted with water and extracted with diethyl ether. The solvent was dried and removed, and the residue was subjected to HPLC with a mixture of hexane and ethyl acetate to give 382 mg of the objective compound.

EXAMPLE 12

Production of
(E)-N-methyl-2-[2-(4-bromophenoxy)phenyl]-2-methoxyiminoacetamide (Compound No. 17)

A solution of (E)-N-methyl-2-(2-phenoxyphenyl)-2-methoxyiminoacetamide (500 mg) in carbon tetrachloride (3 ml) was cooled to 0° C., and bromine in carbon tetrachloride (1.27 mmol) was dropwise added thereto. The resulant mixture was stirred at the same temperature for 1 hour, washed with a saturated aqueous sodium hydrogencarbonate solution and extracted with dichloroethane. The solvent was dried and evaporated, and the residue was subjected to HPLC with a mixture of hexane and ethyl acetate to give 200 mg of the objective compound.

EXAMPLE 13

Production of
(E)-N-methyl-2-(2-phenoxy-5-fluorophenyl)-2-methoxyiminoacetamide (Compound No. 18)

In the same manner as in Example 5, the objective compound was prepared from 4-fluorodiphenyl ether.

EXAMPLE 14

Production of
(E)-N-methyl-2-[2-(4-t-butylphenoxy)phenyl]-2-methoxyiminoacetamide (Compound No. 19)

To a solution of (E)-N-methyl-2-(2-phenoxyphenyl)2-methoxyiminoacetamide (300 mg) in nitromethane (3 ml), aluminium chloride (423 mg) and t-butyl chloride (147 mg) were added, followed by stirring at room temperature for 1 hour. The reaction mixture was diluted with water and extracted with diethyl ether. The solvent was dried and evaporated, and the residue was purified by silica gel column chromatography with a mixture of hexane and ethyl acetate to give 375 mg of the objective compound.

EXAMPLE 15

Production of
(E)-N-methyl-2-[2-(4-methoxyphenoxy)phenyl]-2-methoxyiminoacetamide (Compound No. 22)

(1) To a solution of 4-methoxyphenol (1.50 g) and 2-chloronitrobenzene (1.91 g) in DMF (10 ml), anhydrous potassium carbonate (3.34 g) was added, and the resultant mixture was stirred at 120° C. for 12 hours. The reaction mixture was cooled to room temperature, diluted with water and extracted with diethyl ether. The solvent was dried to give 4-methoxy-2'-nitrodiphenyl ether (2.61 g).

$^1$H-NMR: 3.82 (3H, s), 6.91 (2H, d, J =9.1), 7.02 (2H, d, J =9.1), 7.12 (1H, t, J =8.0), 7.45 (1H, ddd, J =9.1, 8.0, 1.7), 7.92 (1H, dd, J =8.0, 1.7).

(2) The thus obtained 4-methoxy-2'-nitrodiphenyl ether (2.61 g) was dissolved in a mixture of water (30 ml) and toluene (30 ml), and ammonium chloride (5.1 g) and iron powders (1.79 g) were added thereto. The resultant mixture was heated under reflux and vigorously stirred for 4 hours. The reaction mixture was cooled to room temperature, followed by removal of insoluble materials by filtration. The filtrate was extracted with diethyl ether and the solvent was dried and evaporated to give 2-(4-methoxyphenoxy)aniline (2.31 g).

$^1$H-NMR: 3.78 (3H, s), 3.80 (2H, brs), 6.65–6.95 (8H, m).

(3) 2-(4-Methoxyphenoxy)aniline (2.31 g) as obtained (2) above was dissolved in acetic acid (3 ml), followed by addition of conc. hydrobromic acid (3 ml). The resultant mixture was cooled to 0° C. and an aqueous solution (1 ml) of sodium nitrite (741 mg) was further added thereto to make a diazonium salt, which was, without isolation, dropwise added to a solution of copper(I) bromide (918 mg) in conc. hydrobromic acid (2 ml) in another reactor. The resulting mixture was stirred at 100° C. for 2 hours, cooled to room temperature and diluted with water, followed by extraction with diethyl ether. The extract was washed with a saturated aqueous sodium hydrogencarbonate solution. The solvent was dried and evaporated, and the residue was purified by silica gel column chromatography with a mixture of hexane and ethyl acetate to give 4-methoxy-2'-bromodiphenyl ether (1.89 g).

$^1$H-NMR: 3.80 (3H, s), 6.81 - 6.98 (6H, m), 7.21 (1H, t, J =7.3), 7.60 (1H, dd, J =7.9, 1.6).

(4) A solution of 4-methoxy-2'-bromodiphenyl ether (1.19 g) as above obtained in tetrahydrofuran (THF) (20 ml) was cooled to −78° C., and a hexane solution (5.12 mmol) of butyl lithium and hexane was added thereto. The resultant mixture was stirred at the same temperature for 1 hour, followed by addition of dimethyl oxalate (1.01 g) in THF. The mixture was further stirred at room temperature for 2 hours. The reaction mixture was diluted with a saturated ammonium chloride soluiton and extracted with diethyl ether. The solvent was dried and evaporated, and the residue was purified by silica gel column chromatography with a mixture of hexane and ethyl acetate to give methyl 2-[2-(4-methoxyphenoxy)phenyl]-2-oxoacetate (723 mg).

$^1$H-NMR: 3.75 (3H, s), 3.82 (3H, s), 6.80 (1H, d, J =8.3), 6.91 (2H, d, J =9.0), 7.02 (2H, d, J =9.0), 7.16 (1H, t, J =7.8), 7.50 (1H, ddd, J =8.3, 7.8, 1.7), 7.94 (1H, dd, J =7.8, 1.7).

(5) The thus obtained methyl-2-[2-(4-methoxyphenoxy)phenyl]-2-oxoacetate was treated in the same manner as in Example 5 to give the objective compound.

EXAMPLE 16

Production of
(E)-N-methyl-2-[2-(4-trimethylsilylphenoxy)phenyl]-2-methoxyiminoacetamide (Compound No. 28)

In the same manner as in Example 5, the objective compound was prepared from 4-trimethylsilyl diphenyl ether.

EXAMPLE 17

Production of
(E)-N-methyl-2-[2-(4-iodophenoxyphenyl]-2-methoxyiminoacetamide (Compound No. 29)

To a solution of (E)-N-methyl-2-(2-phenoxyphenyl)2-methoxyiminoacetamide (300 mg) in carbon tetrachloride (10 ml), a solution of iodine monochloride (205 mg) in carbon tetrachloride (1 ml) was added, and the resultant mixture was stirred at room temperature for 30 minutes. The reaction mixture was diluted with water and extracted with diethyl ether. The solvent was dried and evaporated, and the residue was subjected to HPLC with a mixture of hexane and ethyl acetate to give 269 mg of the objective compound.

EXAMPLE 18

Production of
(E)-N-methyl-2-[2-(4-chloro-3-methylphenoxy)-phenyl]-2-methoxyiminoacetamide (Compound No. 31)

In the same manner as in Example 11, the objective compound was prepared from (E)-N-methyl-2-[2-(3-tolyloxy)phenyl]-2-methoxyiminoacetamide.

EXAMPLE 19

Production of
(E)-N-methyl-2-[2-(2-tolyloxy)phenyl]-2-methoxyiminoacetamide (Compound No. 32)

In the same manner as in Example 5, the objective compound was prepared from 2-phenoxytoluene.

EXAMPLE 20

Production of
(E)-N-methyl-2-[2-(4-tolyloxy)phenyl]-2-methoxyiminoacetamide (Compound No. 34)

In the same manner as in Example 5, the objective compound was prepared from 4-phenoxytoluene.

EXAMPLE 21

Production of
(E)-N-methyl-2-[2-(4-isopropylphenoxy)phenyl]-2-methoxyiminoacetamide (Compound No. 36)

In the same manner as in Example 14, the objective compound was prepared from 2-chloropropane and (E)-N-methyl-2-(2-phenoxyphenyl)-2-methoxyiminoacetamide.

EXAMPLE 22

Production of
(E)-N-methyl-2-[2-(3,4-dichlorophenoxy)phenyl]-2-methoxyiminoacetamide (Compound No. 38)

In the same manner as in Example 15 (1), the objective compound was prepared from 3,4-dichloro-2'-bromodiphenyl ether.

EXAMPLE 23

Production of
(E)-N-methyl-2-[2-(3-benzyloxyphenoxy)phenyl]-2-methoxyiminoacetamide (Compound No. 39)

In the same manner as in Example 15 (1), the objective compound was prepared from 3-benzyloxy-2'-bromodiphenyl ether.

Example 24

Production of
(E)-N-methyl-2-[2-(3-phenoxyphenoxy)phenyl]-2-methoxyiminoacetamide (Compound No. 41)

In the same manner as in Example 15 (1), the objective compound was prepared from 2-bromo-(3-phenoxyphenoxy)benzene.

EXAMPLE 25

Production of
(E)-N-methyl-2-[2-(4-phenoxyphenoxy)phenyl]-2-methoxyiminoacetamide (Compound No. 42)

In the same manner as in Example 15 (1), the objective compound was prepared from 2-bromo-(4-phenoxyphenoxy)benzene.

EXAMPLE 26

Production of
(E)-N-methyl-2-(benzyloxyphenyl)-2-methoxyiminoacetamide (Compound No. 45)

(1) To a solution of tetrahydropyran-2-yl-phenyl ether (4.19 g) in THF (60 ml), a hexane solution (28.2 mmol) of butyl lithium was added at 0° C., and the resultant mixture was stirred at the same temperature for 2 hours and added to a solution of dimethyl oxalate (5.55 g) in THF (40 ml), followed by stirring for 12 hours. The reaction mixture was neutralized with 1N hydrochloric acid and extracted with diethyl ether. The solvent was dried and evaporated, and the residue was purified by silica gel column chromatography to give methyl-2-(2-tetrahydropyran-2-yl-oxyphenyl)-2-oxoacetate ((3.41 g).

$^1$H-NMR: 1.65–1.86 (6H, m), 3.63–3.75 (1H, m), 3.97–3.92 (1H, m), 3.92 (3H, s), 5.52 (1H, brs), 7.09 (1H, t, J =8.0), 7.27 (1H, d, J =8.0), 7.55 (1H, ddd, J =8.0, 8.0, 1.8), 7.84 (1H, dd, J =8.0, 1.8).

(2) Methyl-2-(2-tetrahydropyran-2-yl-oxyphenyl)-2-oxoacetate (2.60 g) thus obtained was dissolved in methanol (5 ml), and O-methylhydroxylamine hydrochloride (1.70 g) was added thereto. The resultant mixture was heated under reflux for 12 hours. The solvent was removed and the residue was diluted with water and extracted with diethyl ether. Removal of the solvent on drying gave a geometric isomeric mixture of methyl 2-(2-hydroxyphenyl)-2-methoxyiminoacetate, which was then dissolved in DMF (5 ml), followed by addition of anhydrous potassium carbonate (5.26 g) and benzyl bromide (4.34 g) in order. The resultant mixture was stirred at room temperature for 12 hours, diluted with water and extracted with diethyl ether. The solvent was dried and removed, and the residue was purified by silica gel column chromatography with a mixtue of hexane and ethyl acetate to give (Z)-N-methyl-2-(2-benzyloxyphenyl)-2-methoxyiminoacetate (835 mg). The structure of this compound was confirmed by an X-ray crystal analysis.

$^1$H-NMR: 3.36 (3H, s), 4.00 (3H, s), 5.03 (2H, s), 6.94–7.01 (2H, m), 7.33–7.42 (6H, m), 7.73 (1H, dd, J=7.8, 1.9).

(3) (E)-N-Methyl-2-(2-benzyloxyphenyl)-2-methoxyiminoacetate thus obtained was treated in the same manner as in Example 5 to give the objective compound.

EXAMPLE 27

Production of (E)-N-methyl-2-(2-phenoxymethylphenyl)-2-methoxyiminoacetamide (Compound No. 46)

(1) Methyl-(E)-2-(2-tolyl)-2-methoxyiminoacetate (4.74 g) was dissolved in carbon tetrachloride (100 ml), and N-bromosuccinimide (4.89 g) and benzoylperoxide (554 mg) were added thereto. The resultant mixture was heated under reflux for 1 hour and cooled to room temperature. Insoluble materials were removed by filtration. On concentration of the solvent, the residue was purified by silica gel column chromatography with a mixture of hexane and ethyl acetate to give methyl-(E)-2-(2-bromomethylphenyl)-2-methoxyiminoacetate (6.98 g).

$^1$H-NMR: 3.89 (3H, s), 4.07 (3H, s), 4.34 (2H, s), 7.13–7.17 (1H, m), 7.34–7.47 (3H, m).

(2) To a solution of phenol (108 mg) in THF (2 ml), 60% sodium hydride (46 mg) was added, followed by addition of methyl-(E)-2-(2-bromomethylphenyl)-2-methoxyiminoacetate as obtained in (1) above. The resultant mixture was heated under reflux for 8 hours and cooled to room temperature. With addition of an excess methylaminemethanol solution, the mixture was stirred at room temperature for 12 hours and diluted with water, followed by extraction with diethyl ether. The solvent was dried and evaporated, and the residue was purified by silica gel column chromatography with a mixture of hexane and ethyl acetate to give 137 mg of the objective compound.

EXAMPLE 28

Production of (E)-N-methyl-2-[2-(3-phenoxyphenoxymethyl)phenyl]-2-methoxyiminoacetamide (Compound No. 47)

In the same manner as in Example 27, the objective compound was prepared from 3-phenoxyphenol and methyl-(E)-2-(2-bromomethylphenyl)-2-methoxyiminoacetate.

The position of the substituent, steric configuration, melting point (m.p.) and NMR data of the objective compounds as obtained in the preceding examples are shown in Tables 1, 2 and 3 below.

TABLE 1

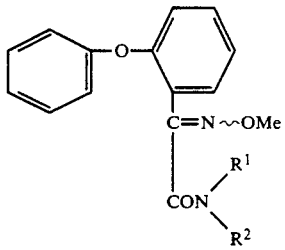

| Compound No. | R$^1$ | R$^2$ | Steric configuration | m.p. (°C.) | $^1$H-NMR δ (CDCl$_3$) (ppm) |
|---|---|---|---|---|---|
| 1 | H | H | | | 3.87(3H, s, CH$_3$), 5.60(1H, brs, NH), 6.33(1H, brs, NH), 6.67–7.50(9H, m, arom.) |
| 2 | CH$_3$ | CH$_3$ | | | 2.77(3H, s, N—CH$_3$), 2.90(3H, s, N—CH$_3$), 3.97(3H, s, O—CH$_3$), 6.63–7.87(9H, m, arom.) |
| 3*) | H | CH$_3$ | E | 65.5–66.5 | 2.78(3H, d, J=5, N—CH$_3$), 3.85 (3H, s, O—CH$_3$), 6.53(1H, brs, NH), 5=6.70–7.47(9H, m, arom.) |
| 4 | H | CH$_3$ | Z | 104.5–105.5 | 2.73(3H, d, J=5, N—CH$_3$), 3.93 (3H, s, O—CH$_3$), 6.27(1H, brs, NH), 6.67–7.67(9H, m, arom.) |

Note: *)Depending on the condition for crystallization, this compound includes transparent needle-like crystals (m.p., 65.5–66.5° C./hexane) and transparent prisms (m.p., 82-5-83° C./ethyl acetate-hexane).

TABLE 2

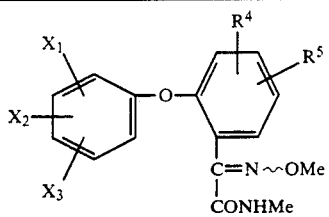

| Compound No. | $X_1, X_2, X_3$ | $R^4, R^5$ | Steric configuration | m.p. (°C.) | $^1$H-NMR δ (CDCl$_3$) (ppm) |
|---|---|---|---|---|---|
| 5 | H, H, 3-Me | H, H | Z | — | 2.31(3H, s), 2.78(3H, d, J=4.9), 4.00(3H, s), 6.31(1H, brs), 6.76–6.92(3H, m), 7.12–7.21(2H, m), 7.29–7.37(2H, m), 7.58(1H, dd, J=7.8, 2.0) |
| 6 | H, H, 3-Me | H, H | E | — | 2.31(3H, s), 2.87(3H, d, J=4.9), 3.91(3H, s), 6.62 1H, brs), 6.80–6.91(4H, m), 7.10–7.21(2H, m), 7.29–7.35(2H, m) |
| 7 | H, H, H, | H, 4-Me | Z | — | 2.31(3H, s), 2.87(3H, d, J=4.9), 3.97(3H, s), 6.23(1H, brs), 6.67(1H, s), 6.90–7.33 (6H, m), 7.49(1H, d, J=7.8) |
| 8 | H, H, H | H, 4-Me | E | 98–100 | 2.31(3H, s), 2.86(3H, d, J=4.9), 3.90(3H, s), 6.61(1H, brs), 6.70(1H, s), 6.83–7.33(7H, m) |
| 9 | H, H, H | H, 6-OMe | E | 106–108 | 2.80(3H, d, J=4.9), 3.75(3H, s), 3.84(3H, s), 6.45(1H, d, J=7.8), 6.64(1H, d, J=7.8), 6.77(1H, brs), 7.00–7.06(3H, m), 7.18–7.28(3H, m) |
| 10 | H, H, H | H, 5-NO$_2$ | E | — | 2.92(3H, d, J=4.9), 4.00(3H, s), 6.80(1H, brs), 6.83(1H, d, J=9.3), 7.10(2H, dd, J=7.3, 1.2), 7.23(1H, t, J=7.3), 7.40(2H, t, J=7.3), 8.16(1H, dd, J=9.3, 2.7), 8.22(1H, d, J=2.7) |
| 11 | H, H, 4-NO$_2$ | H, H | E | 110–112 | 2.85(3H, d, J=4.9), 3.84(3H, s), 6.66(1H, brs), 7.05(2H, d, J=9.3), 7.30–7.47(4H, m), 8.18(2H, d, J=9.3) |
| 12 | H, H, 2-NO$_2$ | H, H | E | — | 2.81(3H, d, J=5.1), 3.90 (3H, s), 6.65(1H, brs), 7.02(1H, d, J=8.81), 7.06 (1H, dd, J=8.3, 1.4), 7.14 (1H, td, J=8.3, 1.2), 7.26 (1H, td, J=7.5, 1.2), 7.22–7.43(2H, m), 7.46(1H, td, J=8.6, 1.7), 7.87(1H, dd, J=8.1, 1.7) |
| 13 | H, H, H | H, 3-NO$_2$ | E | — | 2.76(3H, d, J=5.1), 3.84 (3H, s), 6.81(2H, d, J=7.8), 7.01(1H, t, J=7.3), 7.23 (2H, m), 7.37(1H, t, J=7.8), 7.53(1H, dd, J=7.8, 1.7) |
| 14 | H, H, 4-NO$_2$ | H, 5-NO$_2$ | E | 172–174 | 2.82(3H, d, J=4.9), 4.11 (3H, s), 7.00(1H, d, J=9.0), 7.01(1H, brs), 7.18(2H, d, J=9.0), 8.27(2H, d, J=9.0), 8.27(1H, dd, J=9.0, 2.9), 8.48(1H, d, J=2.9) |
| 15 | H, H, 4-Ac | H, H | E | 112–113 | 2.56(3H, s), 2.85(3H, d, J=4.9), 3.85(3H, s), 6.63(1H, brs), 7.01(1H, m), 7.02(2H, d, J=8.8), 7.24(1H, td, J=7.5, 1.2), 7.37(1H, m), 7.40 (1H, dd, J=7.3, 2.0), 7.91 (2H, d, J=8.8) |
| 16 | H, H, 4-Cl | H, H | E | 108–109 | 2.87(3H, d, J=4.9), 3.90 (3H, s), 6.67(1H, brs), 6.89(1H, d, J=8.5), 6.95 (2H, d, J=9.0), 7.17(1H, td, J=8.5, 1.2), 7.26(2H, d, J=9.0), 7.30–7.38(2H, m) |
| 17 | H, H, 4-Br | H, H | E | 99–101 | 2.83(3H, d, J=4.9), 3.88 3H, s), 6.70(1H, brs), 6.89 (2H, d, J=8.9), 7.15(1H, t, J=7.6), 7.31(2H, d, |

TABLE 2-continued

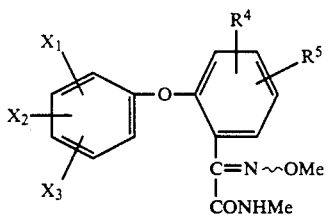

| Compound No. | $X_1, X_2, X_3$ | $R^4, R^5$ | Steric configuration | m.p. (°C.) | $^1$H-NMR δ (CDCl$_3$) (ppm) |
|---|---|---|---|---|---|
| 18 | H, H, H | H, 5-F | E | — | J=7.6), 7.38(2H, d, J=8.9) 2.83(3H, d, J=5.1), 3.88 (3H, s), 6.65(1H, brs), 6.86 (1H, m), 6.95–7.08(5H, m), 7.24–7.32(2H, m) |
| 19 | H, H, 4-tBu | H, H | E | — | 1.31(9H, s), 2.87(3H, d, J= 5.1), 3.93(3H, s), 6.65(1H, brs), 6.88(1H, dd, J=8.3, 1.0), 6.94(2H, d, J=8.8), 7.12(1H, td, J=7.0, 1.0), 7.27–7.32(2H, m), 7.31(2H, d, J=8.8) |
| 20 | H, H, H | H, 5-OMe | Z | — | 2.75(3H, d, J=5.1), 3.83 (3H, s), 3.98(3H, s), 6.15 (1H, brs), 6.85–6.94(3H, m), 7.03(1H, t, J=7.3), 7.14 (1H, d, J=2.7), 7.25–7.30 (2H, m), 7.36(1H, s) |
| 21 | H, H, H | H, 5-OMe | E | — | 2.84(3H, d, J=5.1), 3.80 (3H, s), 3.87(3H, s), 6.57 (1H, brs), 6.83–6.96(5H, m), 6.99–7.04(1H, m), 7.23– 7.29(2H, m) |
| 22 | H, H, 4-OMe | H, H | E | 118 | 2.88(3H, d, J=4.9), 3.79 (3H, s), 3.95(3H, s), 6.70 (1H, brs), 6.79(1H, d, J= 8.6), 6.84(2H, d, J=9.0), 6.98(2H, d, J=9.0), 7.11 (1H, td, J=7.0, 1.0), 7.25–7.31(2H, m) |
| 23 | H, H, H | H, 5-CF$_3$ | E | 111 | 2.90(3H, d, J=5.1), 3.96 (3H, s), 6.74(1H, brs), 6.88 (1H, d, J=8.6), 7.06(2H, d, J=7.6), 7.16(1H, t, J= 7.6), 7.36(2H, t, J=7.6), 7.52–7.57(2H, m) |
| 24 | H, H, H | H, 5-CF$_3$ | Z | 123–124 | 2.82(3H, d, J=4.9), 4.05 (3H, s), 6.68(1H, brs), 6.85 (1H, d, J=8.8), 7.03(2H, d, J=7.5), 7.17(1H, t, J= 7.5), 7.36(2H, t, J=7.6), 7.54(1H, dd, J=8.8, 2.2) |
| 25 | H, H, H | H, 5-SiMe$_3$ | Z | 80–82 | 0.27(9H, s), 2.78(3H, d, J= 4.9), 4.01(3H, s), 6.39(1H, brs), 6.83(1H, d, J=8.1), 7.00(2H, d, J=7.5), 7.09 (1H, t, J=7.5), 7.28–7.31 (2H, m), 7.45(1H, dd, J=8.1, 1.7), 7.68(1H, d, J=1.7) |
| 26 | H, H, 4-SiMe$_3$ | H, H | Z | 103–105 | 0.25(9H, s), 2.78(3H, d, J=4.9), 3.99(3H, s), 6.32(1H, brs), 6.89(1H, dd, J=8.0, 1.1), 6.95 (2H, d, J=8.5), 7.14(1H, td, J=7.6, 1.1), 7.33 (1H, ddd, J=8.0, 7.6, 1.1), 7.45(2H, d, J=8.5), 7.60(1H, dd, J=7.6, 1.7) |
| 27 | H, H, H | H, 5-SiMe$_3$ | E | 86–88 | 0.26(9H, s), 2.87(3H, d, J=4.9), 3.91(3H, s), 6.67(1H, brs), 6.85(1H, d, J=8.10, 7.00–7.11(3H, m), 7.27–7.33(2H, m), 7.42–7.46(2H, m) |
| 28 | H, H, 4-SiMe$_3$ | H, H | E | — | 0.25(9H, s), 2.84(3H, d, J= 4.9), 3.89(3H, s), 6.65(1H, brs), 6.90(1H, dd, J=8.3, 1.5), 6.99(2H, d, J=8.6), 7.14(1H, td, J=7.9, 1.0), |

TABLE 2-continued

Structure: Two phenyl rings connected by O, with X₁, X₂, X₃ substituents on one ring and R⁴, R⁵ on the other ring, which also bears a C(=N~OMe)CONHMe group.

| Compound No. | X₁, X₂, X₃ | R⁴, R⁵ | Steric configuration | m.p. (°C.) | ¹H-NMR δ (CDCl₃) (ppm) |
|---|---|---|---|---|---|
| 29 | H, H, 4-I | H, H | E | 96 | 2.85(3H, d, J=4.9), 3.88 (3H, s), 6.74(1H, brs), 6.77 (2H, d, J=8.8), 6.90(1H, d, J=8.3), 7.16(1H, td, J=8.0, 1.0), 7.30–7.37(2H, m), 7.28–7.34(2H, m), 7.44(2H, d, J=8.6), 7.57(2H, d, J=8.8) |
| 30 | H, H, H | 4-Me, 5-Cl | E | 171–172 | 2.28(3H, s), 2.85(3H, d, J=5.1), 3.91(3H, s), 6.63(1H, brs), 6.75(1H, s), 6.99(2H, d, J=7.3), 7.09(1H, t, J=7.3), 7.25–7.33(3H, m) |
| 31 | H, 4-Cl, 3-Me | H, H | E | — | 2.32(3H, s), 2.87(3H, d, J=4.4), 3.91(3H, s), 6.65(1H, brs), 6.79(1H, dd, J=8.7, 2.8), 6.85–6.89(2H, m), 7.16 (1H, t, J=7.4), 7.25–7.39 (3H, m) |
| 32 | H, H, 2-Me | H, H | E | — | 2.21(3H, s), 2.89(3H, d, J=5.1), 3.95(3H, s), 6.64(1H, brs), 6.68(1H, d, J=8.3), 6.91(1H, d, J=8.1), 7.00–7.32(6H, m) |
| 33 | H, H, H | H, 5-Me | E | — | 2.34(3H, s), 2.87(3H, d, J=5.1), 3.89(3H, s), 6.61(1H, brs), 6.82(1H, d, J=8.3), 6.96–7.00(2H, m), 7.05(1H, t, J=7.3), 7.11(1H, s), 7.14–7.31(3H, m) |
| 34 | H, H, 4-Me | H, H | E | 113–115 | 2.29(3H, s), 2.81(3H, d, J=4.9), 3.89(3H, s), 6.71(1H, brs), 6.82(1H, d, J=8.1), 6.89–6.92(2H, m), 7.05–7.10 (3H, m), 7.23–7.31(2H, m) |
| 35 | H, 2,4-di-(i)Pr | H, H | E | 92–95 | 1.19(6H, d, J=6.8), 1.24 (6H, d, J=7.0), 2.88(3H, d, J=5.1), 2.85(1H, m), 3.20(1H, sept, J=6.8), 3.95(3H, s), 6.67(1H, brs), 6.71(1H, d, J=8.3), 6.82 (1H, d, J=8.3), 6.98(1H, dd, J=8.3, 2.2), 7.06(1H, td, J=7.6, 1.0), 7.13(1H, d, J=2.2), 7.15–7.31(2H, m) |
| 36 | H, H, 4-(i)Pr | H, H | E | — | 1.23(6H, d, J=7.1), 2.86 (3H, d, J=5.1), 2.87(1H, m), 3.92(3H, s), 6.66(1H, brs), 6.84(1H, dd, J=8.3, 1.5), 6.94(2H, d, J=8.4), 7.26–7.32(2H, m), 7.15(2H, d, J=8.4) |
| 37 | H, H, H | 5,6-di-Cl | E | 153 | 2.92(3H, d, J=4.9), 3.96 (3H, s), 6.70(1H, d, J=8.9), 6.73(1H, brs), 7.01–7.09(2H, m), 7.13–7.15(1H, m), 7.29–7.33 (2H, m), 7.37(1H, d, J=8.9) |
| 38 | H, 3,4-di-Cl | H, H | E | 80–81 | 2.88(3H, d, J=4.9), 3.89 (3H, s), 6.62(1H, brs), 6.87 (1H, dd, J=8.6, 2.7), 6.94 (1H, d, J=8.3), 7.11(1H, d, J=2.7), 7.21–7.41(4H, m) |
| 39 | H, H, 3-OCH₂Ph | H, H | E | — | 2.86(3H, d, J=5.1), 3.90 (3H, s), 5.00(2H, s), 6.58–6.73(4H, m), 6.91(1H, d, J=8.3), 7.13–7.42(9H, m) |
| 40 | H, H, 3-OMe | H, H | E | 49–50 | 2.87(3H, d, J=5.1), 3.76 (3H, s), 3.91(3H, s), 6.58–6.65(4H, m), 6.93(1H, d, |

TABLE 2-continued

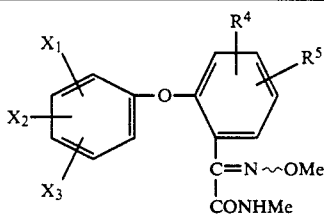

| Compound No. | $X_1, X_2, X_3$ | $R^4, R^5$ | Steric configuration | m.p. (°C.) | $^1$H-NMR δ (CDCl$_3$) (ppm) |
|---|---|---|---|---|---|
| 41 | H, H, 3-OPh | H, H | E | — | J=8.1), 7.12–7.22(2H, m), 7.30–7.36(2H, m) 2.87(3H, d, J=4.9), 3.87 (3H, s), 6.64(1H, brs), 6.70(1H, brs), 6.72(2H, brd, J=7.8), 6.94(1H, d, J=7.8), 7.01(2H, d, J= 7.8), 7.07–7.37(7H, m) |
| 42 | H, H, 4-OPh | H, H | E | — | 2.89(3H, d, J=4.9), 3.94 (3H, s), 6.69(1H, brs), 6.88(1H, d, J=8.8), 6.94– 7.13(8H, m), 7.29–7.35(4H, m) |
| 43 | 5-OPh, 2,4-di-Cl | H, H | E | — | 2.87(3H, d, J=5.1), 3.85 (3H, s), 6.65(1H, brs), 6.70 (1H, s), 6.80(1H, d, J=8.3), 6.90(2H, brd, J=7.8), 7.07 (1H, brt, J=7.5) |

TABLE 3

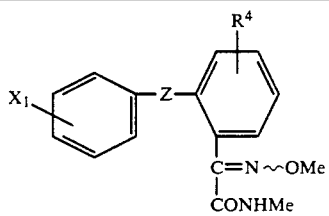

| Compound No. | $X_1$ | $R^4$ | Z | Steric configuration | m.p. (°C.) | $^1$H-NMR δ (CDCl$_3$) (ppm) |
|---|---|---|---|---|---|---|
| 44 | H | H | —CH$_2$O— | Z | 110–111 | 2.65(3H, d, J=4.9), 3.99 (3H, s), 5.03(2H, s), 6.26 (1H, brs), 6.94–7.03(2H, m), 7.34–7.40(6H, m), 7.50(1H, dd, J=7.8, 2.0) |
| 45 | H | H | —CH$_2$O— | E | 123–126 | 2.87(3H, d, J=4.9), 3.93 (3H, s), 5.06(2H, s), 6.61 (1H, brs), 6.97–7.04(2H, m), 7.28–7.39(7H, m) |
| 46 | H | H | —OCH$_2$— | E | 119–120 | 2.89(3H, d, J=4.9), 3.93 (3H, s), 4.95(2H, s), 6.69 (1H, brs), 6.88–6.96(3H, m), 7.20–7.29(3H, m), 7.34– 7.43(2H, m), 7.53–7.54(1H, m) |
| 47 | 3-OPh | H | —OCH$_2$— | E | — | 2.83(3H, d, J=4.9), 3.88 (3H, s), 4.91(2H, s), 6.55– 6.64(3H, m), 6.70(1H, brs), 6.98–7.02(2H, m), 7.09(1H, t, J=7.3), 7.15–7.19(2H, m), 7.21–7.42(4H, m), 7.47– 7.50(1H, m) |
| 48 | 4-Br | H | —OCH$_2$— | E | 137–138 | 2.89(3H, d, J=5.1), 3.92 (3H, s), 4.92(2H, s), 6.76 (2H, d, J=8.8), 7.18–7.21 (1H, m), 7.34(2H, d, J= 8.8), 7.36–8.00(3H, m) |
| 49 | 3-OMe | H | —OCH$_2$— | E | — | 2.87(3H, d, J=4.9), 3.75 (3H, s), 3.92(3H, s), 4.92 (2H, s), 6.45–6.51(3H, m), 6.70(1H, brs), 7.13(1H, d, J=8.1), 7.18–7.24(1H, m), 7.33–7.43(2H, m), |

TABLE 3-continued

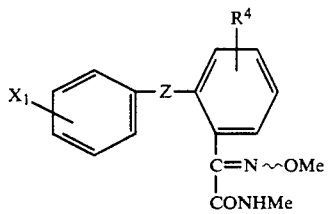

| Compound No. | $X_1$ | $R^4$ | Z | Steric configuration | m.p. (°C.) | $^1$H-NMR δ (CDCl$_3$) (ppm) |
|---|---|---|---|---|---|---|
| | | | | | | 7.49–7.52(1H, m) |

EXAMPLE 29

Production of1N-methyl-2-[2-(3-chlorophenoxymethyl)phenyl]-2-methoxyiminoacetamide (Compound No. 50)

Methyl-(E)-2-(bromomethylphenyl)-2-methoxyiminoacetate as obtained in Example 27 (1) (250 mg), 3-chlorophenol (225 mg) and potassium carbonate (482 mg) were dissolved in DMF, and the resultant mixture was stirred at room temperature for 10 hours. A solution (677 mg) of methylamine in 30 % methanol was added thereto, and stirring was continued for 10 hours. The reaction mixture was neutralized with dilute hydrochloric acid, extracted with diethyl ether. The solvent was dried and evaporated, and the residue was purified by silica gel column chromatography to give 265 mg of the objective compound.

In the same manner as above, Compounds Nos. 50 to 70 as shown in Table 4 below were obtained.

TABLE 4

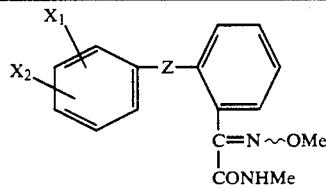

| Compound No. | Z | $X_1$, $X_2$ | Steric configuration | m.p. (°C.) | $^1$H-NMR δ (CDCl$_3$) (ppm) |
|---|---|---|---|---|---|
| 50 | —OCH$_2$— | H, 3-Cl | E | oily | 2.89(3H, d, J=4.9), 3.93(3H, s), 4.93(2H, s), 6.74(1H, brs), 6.78(1H, m), 6.89–6.93(2H, m), 7.15(1H, d, J=7.8), 7.22(1H, m), 7.35–7.50(3H, m) |
| 51 | —OCH$_2$— | H, 2-Cl | E | 126 | 2.87(3H, d, J=5.1), 3.93 (3H, s), 5.05(2H, s), 6.74 (1H, brs), 6.84–6.89(2H, m), 7.14(1H, dt, J=1.5, 7.9), 7.22(1H, dd, J=7.3, 1.7), 7.33–7.44(3H, m), 7.56(1H, brd, J=7.6) |
| 52 | —OCH$_2$— | H, 4-Ph—CH=CH— | E | 215–216 | 2.90(3H, d, J=4.9), 3.94 (3H, s), 4.97(2H, s), 6.71 (1H, brs), 6.88(2H, d, J= 8.8), 6.95(1H, d, J=16.3), 7.05(1H, d, J=16.3), 7.20–7.54(11H, m) |
| 53 | —OCH$_2$— | H, 4-Ph—CO— | E | oily | 2.90(3H, d, J=5.1), 3.94(3H, s), 5.04(2H, s), 6.80(1H, brs), 6.95(2H, d, J=8.8), 7.22(1H, m), 7.41–7.56(6H, m), 7.72–7.75 (2H, m), 7.80(2H, d, J=8.8) |
| 54 | —OCH$_2$— | H, 4-tBu | E | 114 | 1.29(9H, s), 2.88(3H, d, J= 5.1), 3.93(3H, s), 4.92(2H, s), 6.65(1H, brs), 6.82(2H, d, J= 8.7), 7.21(1H, m), 7.27(2H, d, J=8.7), 7.36–7.41(2H, m), 7.52(1H, m) |
| 55 | —OCH$_2$ | H, 4-Me | E | 128–129 | 2.27(3H, s), 2.88(3H, d, J= 4.9), 3.92(3H, s), 4.91(2H, s), 6.69(1H, brs), 6.78(2H, d, J= 8.4), 7.05(2H, d, J=8.4), 7.21(1H, m), 7.35–7.42(2H, m), 7.50(1H, m) |
| 56 | —OCH$_2$ | H, 4-CN | E | 162 | 2.89(3H, d, J=5.1), 3.92(3H, s), 5.01(2H, s), 6.83(1H, brs), 6.94(2H, d, J=8.3), 7.20(1H, m), 7.37–7.48(3H, m), 7.54(2H, |

TABLE 4-continued

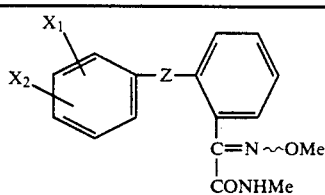

| Compound No. | Z | $X_1$, $X_2$ | Steric configuration | m.p. (°C.) | $^1$H-NMR δ (CDCl$_3$) (ppm) |
|---|---|---|---|---|---|
| | | | | | d, J=8.3) |
| 57 | —OCH$_2$— | H, 2,4-di-Cl | E | 123 | 2.87(3H, d, J=5.1), 3.92(3H, s), 5.03(2H, s), 6.77(1H, brs), 6.78(1H, d, J=8.9), 7.09(1H, dd, J=8.9, 2.7), 7.20(1H, dd, J=7.0, 1.7), 7.33–7.40(3H, m), 7.51(1H, d, J=6.8) |
| 58 | —OCH$_2$— | 3,4-di-Cl | E | 124–126 | 2.89(3H, d, J=5.1), 3.93(3H, s), 4.92(2H, s), 6.74(1H, dd, J=9.0, 2.8), 6.76(1H, brs), 6.98(1H, d, J=2.8), 7.18(1H, m), 7.28(1H, d, J=9.0), 7.36–7.46(3H, m) |
| 59 | —OCH$_2$— | 3,5-di-Cl | E | 102–104 | 2.92(3H, d, J=5.1), 3.95(3H, s), 4.92(2H, s), 6.75(1H, brs), 6.79(2H, d, J=1.7), 6.94(1H, t, J=1.7), 7.20(1H, m), 7.38–7.47(3H, m) |
| 60 | —OCH$_2$— | H, 3-CF$_3$ | E | 69–71 | 2.89(3H, d, J=5.1), 3.92(3H, s), 4.99(2H, s), 6.72(1H, brs), 7.05(1H, dd, J=8.3, 2.0), 7.13(1H, brs), 7.17–7.25(2H, m), 7.33–7.51(4H, m) |
| 61 | —OCH$_2$— | H, 3-Me$_2$N | E | oily | 2.88(3H, d, J=4.9), 2.91(6H, s), 3.93(3H, s), 4.92(2H, s), 6.26–6.28(2H, m), 6.35(1H, dd, J=8.4, 2.2), 6.60(1H, brs), 7.11(1H, t, J=8.4), 7.20(1H, dd, J=9.0, 2.0), 7.37–7.41 (2H, m), 7.52(1H, dd, J=7.0, 2.0) |
| 62 | —OCH$_2$— | H, 3-Br | E | 56–58 | 2.90(3H, d, J=5.1), 3.94(3H, s), 4.93(2H, s), 6.72(1H, brs), 6.82(1H, dt, J=7.6, 2.0), 7.05–7.14(3H, m), 7.20(1H, m), 7.35–7.50(3H, m) |
| 63 | —OCH$_2$— | H, 3-NO$_2$ | E | 127–129 | 2.92(3H, d, J=4.9), 3.95(3H, s), 5.05(2H, s), 6.79(1H, brs), 7.20–7.23(2H, m), 7.37–7.43(3H, m), 7.49(1H, m), 7.73(1H, t, J=2.3), 7.81(1H, dd, J=8.0, 2.3) |
| 64 | —OCH$_2$— | H, 4-F | E | 97 | 2.89(3H, d, J=5.1), 3.93(3H, s), 4.91(2H, s), 6.73(1H, brs), 6.79–6.84(2H, m), 6.90–6.97 (2H, m), 7.20(1H, m), 7.34–7.43 (2H, m), 7.50(1H, m) |
| 65 | —OCH$_2$— | H, 3-(i)PrO | E | oily | 1.31(6H, d, J=6.1), 2.88(3H, d, J=4.9), 3.93(3H, s), 4.50 (1H, sept, J=6.1), 4.91(2H, s), 6.44–6.50(3H, m), 6.68(1H, brs), 7.10–7.22(2H, m), 7.36–7.4(2H, m), 7.51(1H, d, J=6.8) |
| 66 | —OCH$_2$— | H, 4-Cl | E | 132–133 | 2.90(3H, d, J=4.9), 3.93(3H, s), 4.92(2H, s), 6.72(1H, brs), 6.81(2H, d, J=9.0), 7.20(1H, m), 7.20(2H, d, J=9.0), 7.37–7.49(3H, m) |
| 67 | —SCH$_2$— | H, H | E | oily | 2.90(3H, d, J=5.1), 3.95(3H, s), 3.99(2H, s), 6.75(1H, brs), 7.14–7.31(9H, m) |
| 68 | —SOCH$_2$— | H, H | E | oily | 2.94(3H, d, J=4.9), 3.76(1H, d, J=12.5), 3.98(3H, s), 4.24 (1H, d, J=12.5), 6.73(1H, d, J=7.8), 7.03(1H, brs), 7.14–7.20(2H, m), 7.30–7.45(6H, m) |
| 69 | —OCH$_2$— | H, 4-Cl | Z | 162–163 | 2.90(3H, d, J=4.9), 3.98 (3H, s), 5.17(2H, s), 6.64(1H, brs), 6.85(2H, brd, J=8.9), |

TABLE 4-continued

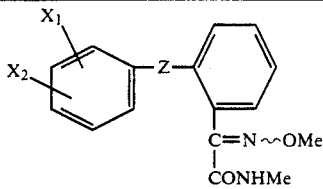

| Compound No. | Z | $X_1, X_2$ | Steric configuration | m.p. (°C.) | $^1$H-NMR δ (CDCl$_3$) (ppm) |
|---|---|---|---|---|---|
| 70 | —OCH$_2$— | H, 3-(i)PrO | Z | oily | 7.23(2H, brd, J=8.9), 7.36–7.52(4H, m) 1.32(6H, d, J=6.1), 2.87(3H, d, J=4.9), 3.95(3H, s), 4.50 (1H, sept, J=6.1), 5.16(2H, s), 6.49–6.52(2H, m), 6.67(1H, brs), 7.12–7.54(6H, m) |

EXAMPLE 30

Production of N-methyl-2-[2-(3-methyl-2-butenyloxy)phenyl]-2-methoxyiminoacetamide (Compound No. 71)

(1) A solution of 2-bromophenol (10.0 g), dihydropyrane (7.28 g) and pyridinium p-toluenesulfonate (PPTS) (725 mg) in dichloromethane was stirred at room temperature for 10 hours. After removal of the solvent and excess dihydropyrane, the reaction mixture was diluted with THF (150 ml), followed by cooling to −78° C. n-Butyl lithium (1.6M; 47 ml) was dropwise added thereto, and the mixture was stirring for 30 minutes. Dimethyl oxalate (13.6 g) was added to the mixture at the same temperature and stirring was continued for 2 hours. The reaction mixture was diluted with water and extracted with ether, followed by removal of the solvent on drying. The residue was dissolved in methanol (100 ml) and combined with O-methyl hydroxylamine hydrochloride (7.24 g), followed by heating under reflux for 4 hours. The reaction mixture was allowed to cool to room temperature and, after removal of methanol, diluted with water, followed by extraction with ethyl acetate. The solvent was dried and distilled off, and the residue was dissolved in 30% methanolic methylamine (23 g). The resultant mixture was stirred for 10 hours and methylamine was removed therefrom. The residue was purified by silica gel column chromatography, whereby 3.23 g of E-isomer and 6.87 g of Z-isomer of N-methyl-[2-(2-hydroxy)phenyl]-2-methoxyiminoacetamide were obtained.

E-isomer $^1$H-NHR: 3.90 (3H, s), 4.15 (3H, s), 6.14 (1H, brs), 6.96–7.01 (2H, m), 7.24 (1H, dd, J =8.3, 1.7), 7.35 (1H, brt, J =8.3).

(2) The above obtained E-isomer (200 mg), prenyl bromide (286 mg) and potassium carbonate (265 mg) was dissolved in DMF, and the resultant solution was stirred at room temperature for 2 hours. The reaction mixture was neutralized with dilute hydrochloric acid, extracted with ethyl acetate and purified by silica gel column chromatography to give 286 mg of the objective compound.

In the same manner as above, Compounds Nos. 71 to 74 as shown in Table 5 below were obtained.

TABLE 5

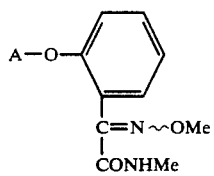

| Compound No. | A | Steric configuration | m.p. (°C.) | $^1$H-NMR δ (CDCl$_3$) (ppm) |
|---|---|---|---|---|
| 71 | CH$_3$\C=CHCH$_2$—/CH$_3$ | E | 48–50 | 1.69(3H, s), 1.75(3H, s), 2.90 (3H, d, J=4.9), 3.94(3H, s), 4.50(2H, d, J=6.6), 5.37(1H, t, J=6.6), 6.64(1H, brs), 6.94 (1H, dd, J=8.1, 1.0), 6.99(1H, dd, J=7.6, 1.0), 7.23(1H, dd, J= 7.6, 1.7), 7.33(1H, ddd, J=8.1, 7.6, 1.7) |
| 72 | CH$_3$\C=CH(CH$_2$)$_2$C(CH$_3$)=CHCH$_2$—/CH$_3$ | E | oily | 1.60(3H, s), 1.68(6H, s), 2.91 (3H, d, J=4.9), 3.94(3H, s), 4.53(2H, d, J=5.1), 5.08(1H, t, J=5.1), 5.38(1H, t, J= 5.1), 6.64(1H, brs), 6.94(1H, d, J=8.3), 6.99(1H, dd, J= 7.6, 1.0), 7.23(1H, dd, J= 7.6, 1.7), 7.34(1H, ddd, J= 8.3, 7.6, 1.7) |

TABLE 5-continued

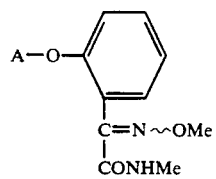
C=N~OMe
|
CONHMe

| Compound No. | A | Steric configuration | m.p. (°C.) | $^1$H-NMR δ (CDCl$_3$) (ppm) |
|---|---|---|---|---|
| 73 | Cl\C=CHCH$_2$—/Cl | E | 41 | 2.93(3H, d, J=4.9), 3.96 (3H, s), 4.66(2H, d, J=6.1), 6.07(1H, t, J=6.1), 6.71(1H, brs), 6.91(1H, brd, J=8.3), 7.04(1H, brt, J=8.3), 7.23 (1H, dd, J=7.6, 1.7), 7.38 (1H, ddd, J=8.3, 7.6, 1.7), |
| 74 | Cl\C=CHCH$_2$—/Cl | Z | 112 | 2.96(3H, d, J=4.9), 4.02 (3H, s), 6.87(1H, d, J=7.9), 7.02(1H, t, J=7.6), 7.37 (1H, td, J=7.9, 1.7), 7.49 (1H, dd, J=7.6, 1.7) |

EXAMPLE 31

Production of N-methyl-2-[2-(pyrimidin-2-yloxy-methyl)phenyl]-2-methoxyiminoacetamide (Compound No. 79)

(1) Methyl-2-(2-bromomethylphenyl)-2-methoxyiminoacetate (2.00 g) and potassium acetate (1.37 g) were suspended in THF, and the suspension was heated under reflux for 3 hours. The reaction mixture was cooled to room temperature, and 30 % methanolic methylamine (5.4 g) was added thereto. The resultant mixture was stirred for 10 hours, diluted with water and neutralized, followed by extraction with ethyl acetate. The solvent was dried and distilled off, and the residue was purified by silica gel column chromatography, whereby there was obtained (E) N-methyl-2-(2-hydroxymethylphenyl)-2-methoxyiminoacetamide (1.05 g).

$^1$H-NMR: 2.92 (3H, d, J =4.9), 3.22 (1H, t, J =4.9), 3.95 (3H, s), 4.39 (2H, d, J =4.9), 6.97 (1H, brs), 7.13 (1H, brd, J =7.6), 7.35 (1H, td, J =7.6, 1.5), 7.42 (1H, td, J =7.6, 1.5), 7.52 (1H, brd, J =7.6).

(2) N-methyl-2-(2-hydroxymethylphenyl)-2-methoxyiminoacetamide as obtained in (1) above (300 mg), 2-chloropyrimidine (233 mg) and sodium hydride (40%; 135 mg) were dissolved in DMF, and the resultant mixture was stirred at 100° C for 6 hours. After neutralization, the reaction mixture was diluted with water and extracted with dichloromethane. The solvent was dried and evaporated, and the residue was purified by silica gel column chromatography to give 70 mg of the objective compound.

EXAMPLE 32

Production of (E) N-methyl-2-(2-phenylthiophenyl)-2-methoxyiminoacetamide (Compound No. 82)

The objective compound was prepared in the same manner as in Example 5 but using phenylsulfide in place of 3-phenoxytoluene.

EXAMPLE 33

Production of (E) N-methyl-2-(2-phenylsulfinylmethylphenyl)-2-methoxyiminoacetamide (Compound No. 68)

The objective compound was produced by oxidation of Compound No. 67 with sodium metaperiodate.

EXAMPLE 34

Production of (E)-N-methyl-2-(5-trifluoromethylpyridyl-2-oxyphenyl)-2-methoxyiminoacetamide (Compound No. 75)

(1) To a solution of 2-bromophenol (3.46 g) in DMF (10 ml), potassium carbonate (5.53 g) and 2-chloro-5-trifluoromethyl pyridine (7.26 g) were added, and the resultant mixture was stirred at 60° C, followed by cooling. Water was added the reaction mixture, which was extracted with dichloromethane. The extract was dried over anhydrous sodium sulfate and purified by silica gel column chromatograpy to give 2-(5-trifluoromethylpyridyl-2-oxy-bromobenzene (2.70 g).

(2) 2-(5-trifluoromethylpyridyl-2-oxy)-bromobenzene obtained in (1) above (2.62 g) was dissolved in THF (20 ml). Under argon stream, 1.6 M hexane solution (6.2 ml) of n-butyl lithium was dropwise added thereto at −78° C. in 2 minutes, and the resultant mixture was stirred for 5 minutes. A solution of dimethyl oxalate (1.95 g) in THF (20 ml) was added thereto at once, and thereafter warmed to room temperature, followed by stirring for 20 minutes. Aqueous ammonium chloride was added to the reaction mixture and, after removal of THF, extraction with dichloromethane was performed. The residue was washed with water and dried over anhydrous sodium sulfate. After removal of the solvent, the residue was purified by silica gel column chromatography to afford methyl-2-(5-trifluoromethylpyridyl-2-oxyphenyl)-2-oxoacetate (1.68 g).

(3) Methyl-2-(5-trifluoromethylpyridyl-2-oxyphenyl)-2-oxoacetate (1.21 g) as obtained (2) was dissolved in methanol (10 ml), and O methyl hydroxylamine (0.74 g) was added thereto. The resultant mixture was refluxed for 2 hours, followed by removal of methanol. Water was added to the mixture, which was extracted with dichloromethane. The residue was dried over anhydrous sodium sulfate and, after removal of the solvent, purified by silica gel column chromatography to give methyl-2-(5-trifluoromethylpyridyl-2-oxyphenyl)-2-methoxyiminoacetate in a mixture of Z-isomer (0.2 g) and E-isomer (0.60 g).

(4) The E-isomer (0.60 g) was dissolved in methanol (10 ml), and 30 % methanolic methyl amine (0.35 g) was dropwise added thereto. The resultant mixture was refluxed for 20 minutes, and after removal of methanol, the residue was purified by silica gel column chromatography and recrystallized from n-hexane to give 0.50 g of the objective compound.

In the same manner as above, Compounds No. 75 to 77 as shown in Table 6 below were obtained.

EXAMPLE 35

Production of (E)-N-methyl-2-(5-trifluoromethylpyridyl-2-oxymethylphenyl)-2-methoxyiminoacetamide (Compound No. 78)

To a solution of (E)-N-methyl-2-(2-hydroxymethylphenyl)-2-methoxyiminoacetamide (0.10 g) in THF (10 ml), sodium hydride (60% oily suspension) (0.02 g) was added thereto, and the resultant mixture was stirred at room temperature for 10 minutes. To the reaction mixture, 2-chloro-5-trifluoromethylpyridine (0.10 g) was added, and stirring was continued at 60° C. for 1 hour. The reaction mixture was cooled, diluted with water, followed by extraction with dichloromethane. The sol-

TABLE 6

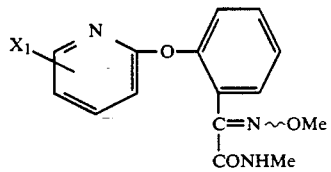

| Compound No. | $X_1$ | Steric configuration | m.p. (°C.) | $^1$H-NMR δ (CDCl$_3$) (ppm) |
|---|---|---|---|---|
| 75 | 5-CF$_3$ | E | 100–100.5 | 2.83(3H, d, J=4.9), 3.78(3H, s), 6.59(1H, brs), 6.97(1H, d, J=8.8), 7.20–7.50(4H, m), 7.87(1H, dd, J=8.8, 2.9), 8.43(1H, d, J=2.9) |
| 76 | 3-CF$_3$ | E | 134.5–135.5 | 2.84(3H, d, J=4.9), 3.74(3H, s), 6.58(1H, brs), 7.06(1H, m), 7.26–7.51(4H, m), 7.96(1H, d, J=6.4), 8.25(1H, d, J=3.7) |
| 77 | 5-CF$_3$ | Z | 85.5–86.5 | 2.75(3H, d, J=4.9), 3.91(3H, s), 6.25(1H, brs), 6.99(1H, d, J=8.8), 7.15(1H, d, J=7.8), 7.30(1H, m), 7.47(1H, m), 7.66(1H, dd, J=7.8, 2.0), 7.90(1H, dd, J=8.8, 2.7), 8.42(1H, brs) | vent was dried over anhydrous sodium sulfate, and after removal of the solvent, purified by silica gel colum chromatography and recrystallized from n-hexane to give 0.11 g of the objective compound.

In the same manner as above, Compounds Nos. 78 to 81 as shown in Table 7 were obtained:

TABLE 7

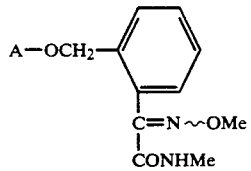

| Compound No. | A | Steric configuration | m.p. (°C.) | $^1$H-NMR δ (CDCl$_3$) (ppm) |
|---|---|---|---|---|
| 78 | F$_3$C—⟨pyridyl⟩ | E | 85.6–86 | 2.89(3H, d, J=4.9), 3.92(3H, s), 5.30(2H, s), 6.76(1H, brs), 6.78(1H, d, J=8.8), 7.21(1H, m), 7.35–7.41 (2H, m), 7.53(1H, m), 7.74(1H, dd, J= 8.8, 2.9), 8.38(1H, d, J=2.9) |
| 79 | ⟨pyrimidinyl⟩ | E | oily | 2.93(3H, d, J=4.9), 3.92(3H, s), 5.31(2H, s), 6.90(1H, t, J=4.6), 6.92(1H, brs), 7.25(1H, dd, J= 7.5, 2.0), 7.33–7.42(2H, m), 7.61 (1H, dd, J=8.0, 2.0), 8.45(2H, d, J=4.6) |

TABLE 7-continued $$\text{A}-\text{OCH}_2-\underset{\underset{\text{CONHMe}}{|}}{\overset{\text{C}=\text{N}\sim\text{OMe}}{\bigcirc}}$$

| Compound No. | A | Steric configuration | m.p. (°C.) | $^1$H-NMR δ (CDCl$_3$) (ppm) |
|---|---|---|---|---|
| 80 | (pyridin-2-ylmethyl) | E | 74–75 | 2.89(3H, d, J=5.1), 3.92(3H, s), 5.24(2H, s), 6.71(1H, d, J=8.1), 6.72(1H, brs), 6.85(1H, dd, J=6.1, 5.1), 7.23(1H, m), 7.36–7.41 (2H, m), 7.51–7.58(2H, m), 8.11 (1H, dd, J=5.1, 2.0) |
| 81 | (pyridin-2-ylmethyl) | Z | 107–108 | 2.90(3H, d, J=4.9), 3.91(3H, s), 5.50(2H, s), 6.77(1H, d, J=8.3), 6.86(1H, m), 6.95(1H, brs), 7.32–7.41(2H, m), 7.47–7.62(3H, m), 8.10(1H, dd, J=5.1, 2.0) |

EXAMPLE 36

Production of (E)-N-methyl-2-[2-(3-hydroxyphenoxy)phenyl]-2-methoxyiminoacetamide (Compound No. 83)

(1) In the same manner as in Example 15, 3-(2-bromophenoxy)phenol was prepared from resolcinol and 2-chloronitrobenzene.

(2) To a solution of 3-(2-bromophenoxy)phenol as obtained above (6.12 g) in dichloromethane (120 ml), dihydropyran (3.16 ml) and PPTS (0.1 g) were added, and the resultant mixture was stirred at room temperature for 1 hour. Th reaction mixture was diluted with dichloromethane and washed with saturated sodium hydrogen carbonate solution. The solvent was dried and removed, and the residue was purified by silica gel chromatography to give 3-(2-bromophenoxy)phenol tetrahydropyranyl ether (7.18 g).

(3) A solution of 3-(2-bromophenoxy)phenyl tetrahydropyranyl ether obtained in (2) above (7.18 g) in THF (120 ml) was cooled to −78° C., and a solution of butyl lithium-hexane (1.6 M, 12.8 ml) was dropwise added thereto. The resultant mixture was stirred at the same temperaature for 30 minutes, and a solution of dimethyl oxalate (4.86 g) in THF (40 ml) was added thereto. Stirring was continued at room temperature for 2 hours. The reaction mixture was diluted with water and extracted with ether. The solvent was dried and removed, and the residue was dissolved in methanol (100 ml). 0-Methyl hydroxylamine hydrochloride (2.58 g) was added to the solution, which was refluxed for 3 hours. The reaction mixture was cooled to room temperature and methanol was removed therefrom, followed by dilution with water. The dilute mixture was extracted with ethyl acetate. The solvent was removed and the residue was purified by silica gel column chromatography to give methyl-2-[2-(3-hydroxyphenoxy)phenyl]-2-methoxyiminoacetate in a mixture of Z-isomer (1.48 g) and E-isomer (2.57 g).

(4) The product as obtained above was treated in the same manner as in Example 5 (3) to give the objective compound.

EXAMPLE 37

Production of (E)-N-methyl-2-[2-(3-tetrahydropyran-2-yloxyphenoxy)phenyl]-2-methoxyiminoacetamide (Compound No. 84)

To a solution of methyl-2-[2-(3-hydroxyphenoxy)phenyl]-2-methoxyiminoacetate (0.25 g) in dichloromethane (10 ml), dihydropyrane (0.3 ml) and PPTS (20 mg) were added, and the resultant mixture was stirred at room temperature for 2 hours. The reaction mixture was diluted with dichloromethane, washed with a saturated aqueous sodium hydrogencarbonate solution, followed by removal of the solvent. The residue was dissolved in methanol (3 ml), and 40% methanolic methylamine (0.5 ml) was added thereto. The resultant mixture was stirred at room temperature for 15 hours. The solvent and excess methylamine were removed, and the residue was purified by silica gel column chromatography to give 0.27 g of the objective compound.

EXAMPLE 38

Production of (E)-N-methyl-2]-2-[3-(1,3-benzothiazol-2-yloxy)-phenoxy]phenyl,-2 -methoxyiminoacetamide (Compound No. 90)

To a solution of (E)-N-methyl-2-[2-(3-hydroxyphenoxy)phenyl]-2-methoxyiminoacetamide (0.21 g) in DMF (3 ml), sodium hydride (34 mg) and 2-chloro-1,3-benzothiazole (0.18 g) were added, and the resultant mixture was stirred at 60° C. for 1 hour. The reaction mixture was cooled to room temperature, diluted with water and extracted with ether. The solvent was dried and the residue was purified by silica gel column chromatography to give 0.27 g of the objective compound.

EXAMPLE 39

Production of (E)-N-methyl-2-[2-(3-benzoyloxyphenoxy)phenyl]-2-methoxyiminoacetamide (Compound No. 94)

To a solution of (E)-N-methyl-2-[2-(3-hydroxyphenoxy)phenyl]-2-methoxyiminoacetamide (0.21 g) in dichloromethane (5 ml), benzoyl chloride (0.12 g) and triethylamine (0.20 g) were added, and the resultant mixture was stirred at room temperature for 30 minutes. The reaction mixture was diluted with ether, washed with dilute hydrochloric acid and a saturated aqueous sodium hydrogen carbonate solution. The solvent was dried and removed, and the residue was purified by silica gel column chromatography to give 0.27 g of the objective compound.

EXAMPLE 40

Production of (E)-N-methyl-2-{2-[3-(3-metoxyphenoxy)phenoxy]-phenyl{-2-methoxyiminoacetamide (Compound No. 87)

In the same manner as in Example 15, the objective compound was prepared from 3-(3-methoxyphenoxy)-phenol and 2-chloronitrobenzene.

In the same manner as above, Compounds Nos. 82 to 102 as shown in Table 8 below were obtained.

TABLE 8

$$X_1 \text{—} \bigcirc \text{—} Z \text{—} \bigcirc \text{—} \underset{\underset{CONHMe}{|}}{C=N\sim OMe}$$

| Compound No. | Z | $X_1$ | Steric configuration | m.p. (°C.) | δ $^1$H—NMR (CDCl$_3$) (ppm) |
|---|---|---|---|---|---|
| 82 | S | H | E | 105–107 | 2.90(3H, d, J=5.1), 3.87 (3H, s), 6.69(1H, brs), 7.17–7.41(9H, m) |
| 83 | O | 3-OH | E | 157–159 | 2.84(3H, d, J=5.9), 3.91 (3H, s), 6.42(1H, t, J= 2.0), 6.48–6.53(2H, m), 6.75(2H, brs), 6.90(1H, d, j=8.8), 7.05–7.33(4H, m) |
| 84 | O | 3-O-(tetrahydropyranyl) | E | oily | 1.59–2.04(6H, m), 2.87(3H, d, J=4.90), 3.58(1H, brd), 3.90(1H), 3.91(3H, s), 5.36(1H, t, J=3.9), 6.61– 6.80(5H, m), 6.93(1H, d, J=7.8), 7.15–7.35(4H, m) |
| 85 | O | 3-O-pyrimidinyl | E | oily | 2.84(3H, d, J=4.9), 3.87 (3H, s), 6.69(1H, brs), 6.84–7.35(9H, m), 8.56(2H, d, J=4.9) |
| 86 | O | 3-O-(CF$_3$-pyridinyl) | E | 110–113 | 2.85(3H, d, J=4.9), 3.87 (3H, s), 6.71(1H, brs), 6.81–7.03(5H, m), 7.18(1H, brt, J=6.8), 7.30–7.40 (3H, m), 7.90(1H, dd, J= 2.0, 8.8), 8.43(1H, brs) |
| 87 | O | 3-O-(3-OCH$_3$-phenyl) | E | oily | 2.88(3H, d, J=4.9), 3.78 (3H, s), 3.87(3H, s), 6.57– 6.75(7H, m), 6.95(1H, d, J=8.8), 7.15–7.34(5H, m) |
| 88 | O | 3-O-(2-O$_2$N-phenyl) | E | oily | 2.87(3H, d, J=4.9), 3.87 (3H, s), 6.64–6.79(4H, m), 6.98(1H, d, J=7.8), 7.10 (1H, d, J=7.8), 7.15–7.40 (5H, m), 7.53(1H, t, J= 8.8), 7.95(1H, d, J=6.8) |
| 89 | O | 3-O-quinolinyl | E | oily | 2.75(3H, d, J=4.9), 3.82 (3H, s), 6.77(1H, d, J= 8.8), 6.94–7.46(10H, m), 7.63(1H, t, J=6.8), 6.77 (1H, d, J=7.8), 7.85(1H, d, J=8.8), 8.14(1H, J= 8.8) |

TABLE 8-continued

Structure: X₁—(phenyl)—Z—(phenyl)—C(=N~OMe)—CONHMe

| Compound No. | Z | X₁ | Steric configuration | m.p. (°C.) | δ ¹H—NMR (CDCl₃) (ppm) |
|---|---|---|---|---|---|
| 90 | O | 3-O-(benzothiazol-2-yl) | E | oily | 2.84(3H, d, J=4.9), 3.86 (3H, s), 6.77(1H, brs), 6.89(1H, dd, J=2.0, 8.8), 7.03-7.43(9H, m), 7.69(1H, d, J=8.8), 7.73(1H, d, J=8.8) |
| 91 | O | 3-OCH₂C(=O)Ph | E | oily | 2.84(3H, d, J=4.9), 3.88 (3H, s), 5.25(2H, s), 6.59-6.71(4H, m), 6.94(1H, d, J=7.8), 7.12-7.62(7H, m), 7.98(2H, d, J=8.8) |
| 92 | O | 3-OSO₂—(4-CH₃-C₆H₄) | E | oily | 2.45(3H, s), 2.86(3H, d, J=4.9), 3.85(3H, s), 6.66-6.89(5H, m), 7.15-7.34(6H, m), 7.72(2H, d, J=8.8) |
| 93 | O | 3-OCOCH₃ | E | 97-98.5 | 2.26(3H, s), 2.85(3H, d, J=4.9), 3.88(3H, s), 6.65 (1H, brs), 6.73-6.88(3H, m), 6.98(1H, d, J=8.8), 7.15-7.38(4H, m) |
| 94 | O | 3-OCOPh | E | oily | 2.87(3H, d, J=5.8), 3.89 (3H, s), 6.69(1H, brs), 6.88-7.04(4H, m), 7.16-7.40(5H, m), 7.50(2H, t, J=7.8), 7.63(1H, t, J=7.9), 8.17(2H, d, J=6.8) |
| 95 | O | 3-OCH₂—(2-NC-C₆H₄) | E | oily | 2.87(3H, d, J=4.9), 3.91 (3H, s), 5.03(2H, s), 6.61-6.71(4H, m), 6.91(1H, d, J=8.8), 7.14-7.71(8H, m) |
| 96 | O | 3-OCH₂C≡CH | E | 80-81 | 2.50(1H, t, J=2.0), 2.87 (3H, d, J=5.9), 3.91(3H, s), 4.64(2H, d, J=2.0), 6.61-6.73(4H, m), 6.95(1H, d, J=7.9), 7.13-7.37(4H, m) |
| 97 | O | 3-CH=CH—Ph | E | oily | 2.85 and 2.87(total 3H, d, J=4.9), 3.85 and 3.91 (total 3H, s), 6.56-7.50 (16H, m) |
| 98 | O | 3-CH=CH—(furan-2-yl) | E | oily | 2.87(3H, d, J=4.9), 3.87 and 3.90(total 3H, s), 6.27-7.39(14H, m) |
| 99 | O | 4-OH | E | 198 | 2.89(3H, d, J=5.1), 3.95(3H, s), 6.65(1H, brs), 6.76-6.81(3H, m), 6.91-6.95(2H, m), 7.09 (1H, m), 7.26-7.29(2H, m) |
| 100 | O | 4-OCH₂Ph | E | 130-131 | 2.88(3H, d, J=5.1), 3.94 (3H, s), 5.04(2H, s), 6.65 (1H, brs), 6.80(1H, dd, J=8.6, 1.2), 6.92(2H, d, J=9.3), 7.09(1H, brt, J=7.1), 7.27-7.45(7H, m) |

TABLE 8-continued

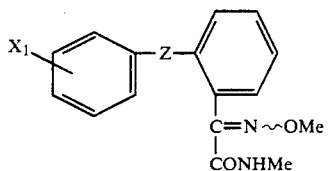

| Compound No. | Z | X₁ | Steric configuration | m.p. (°C.) | δ ¹H—NMR (CDCl₃) (ppm) |
|---|---|---|---|---|---|
| 101 | O | 3-O-[pyridyl]-CF₃ | Z | oily | 2.78(3H, d, J=4.9), 3.97 3H, s), 6.42(1H, brs), 6.77 (1H, t, J=2.4), 6.86(2H, m), 7.01(2H, m), 7.18(1H, dt, J=1.2, 7.6), 7.31–7.40(2H, m), 7.62(1H, dd, J=1.7, 7.6), 7.90(1H, dd, J=2.2, 8.5), 8.41(1H, brs) |
| 102 | O | 3-OCH₂Ph | Z | oily | 2.77(3H, d, J=4.9), 3.99 (3H, s), 5.01(2h, s), 6.25 (1H, brs), 6.56(1H, dd, J=1.7, 7.6), 6.61(1H, t, J=2.4), 6.72(1H, dd, J=1.7, 8.3), 6.88(1H, dd, J=1.2, 8.3), 7.14(1H, dt, J=1.0, 7.6), 7.19 (1H, t, J=8.3), 7.29–7.41(6H, m), 7.60(1H, dd, J=1.7, 7.6) |

EXAMPLE 41

Production of (E)-N-methyl-2-[2-(3-methylanilinomethyl)phenoxyphenyl]-2-methoxyiminoacetamide (Compound No. 104):

(1) To a solution of (E)-methyl-2-[2-(3-methylphenoxy)phenyl]-2-methoxyiminoacetate (4.60 g) in benzene (120 ml), N-bromosuccinimide (2.88 g) and benzoyl peroxide (0.37 g) were added, and the resultant mixture was refluxed for 1 hour, followed by cooling to room temperature. Insoluble materials were removed by filtration and, after removal of the solvent, the residue was purified by silica gel column chromatography to give (E)-methyl-2-[2-(3-bromomethylphenoxy)phenyl]-2-methoxyiminoacetate (4.60 g).

(2) The above obtained product (0.30 g) was dissolved in DMF (4 ml), and N-methylaniline (0.13 ml) and potassium carbonate (0.16 g) were added thereto, followed by stirring at room temperature for 4 hours. The reaction mixture was diluted with water and extracted with ether. The solvent was dried and the residue was combined with 40% methanolic methylamine (1 ml), followed by stirring at room temperature for 3 hours. The solvent was removed and the residue was purified by silica gel column chromatography to give 0.31 g of the objective compound.

EXAMPLE 42

Production of (E)-N-methyl-2-[2-[3-(2-pyridyloxy)phenoxy]phenyl]-2-methoxyiminoacetamide (Compound No. 105)

A solution of (E)-methyl-2-[2-(3-bromomethylphenoxy)phenyl]-2-methoxyiminoacetate (0.50 g), 2-hydroxypyridine (0.15 g) and silver carbonate (0.22 g) in hexane (10 ml) was heated under reflux for 4 hours, followed by removal of hexane. The reaction mixture was diluted with dichloromethane, and insoluble materials were removed by filtration. After removal of the solvent, the residue was combined with 40 % methanolic methylamine (2 ml) and stirred at room temperature for 4 hours. Methylamine was removed and the residue was purified by silica gel column chromatography to give 0.38 g of the objective compound.

EXAMPLE 43

Production of (E)-N-methyl-2-2-[3-pyrimidin-2yloxymethyl)phenoxy]phenyl -2-methoxyiminoacetamide (Compound No. 106)

The objective compound was prepared from (E)-methyl-2-[2-(3-bromomethylphenoxy)phenyl]-2-methoxyiminoacetate in the same manner as in Example 31.

In the same manner as above, Compounds Nos. 103 to 112 as shown in Table 9 were obtained.

TABLE 9

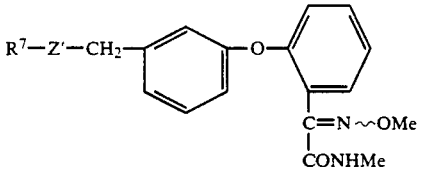

| Compound No. | R⁷ | Z' | Steric configuration | m.p. (°C.) | $^1$H—NMR δ (CDCl$_3$) (ppm) |
|---|---|---|---|---|---|
| 103 | Ph | S | E | oily | 2.85(3H, d, J=4.9), 3.88(3H, s), 4.06(2H, s), 6.61(1H, brs), 6.80(1H, d, J=7.8), 6.86(1H, brd, J=7.8), 6.96(1H, brs), 7.03 (1H, d, J=7.8), 7.11-7.34(9H, m) |
| 104 | Ph | NCH$_3$ | E | oily | 2.84(3H, d, J=5.9), 3.02(3H, s), 3.86(3H, s), 4.48(2H, s), 6.59(1H, brs), 6.72(2H, d, J=7.8), 6.85-6.97(4H, m), 7.12-7.37(7H, m) |
| 105 | 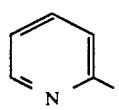 | O | E | oily | 2.86(3H, d, J=4.9), 3.89(3H, s), 5.34(2H, s), 6.61(1H, brs), 6.80(1H, d, J=8.8), 6.86-6.95 (3H, m), 7.14-7.35(6H, m), 7.58 (1H, dt, J=2.0, 6.8), 8.16(1H, dd, J=2.0, 4.9) |
| 106 | Ph | S=O | E | oily | 2.86(3H, d, J=5.9), 3.90(3H, s), 3.94, 4.02(each 1H, ABq, 11.7), 6.70-6.81(4H, m), 6.92 (1H, dd, J=2.0, 7.8), 7.16-7.47(9H, m) |
| 107 | 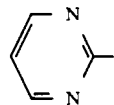 | O | E | oily | 2.86(3H, d, J=5.1), 3.88(3H, s), 5.39(2H, s). 6.64(1H, brs), 6.89-6.97(3H, m), 7.12-7.37(6H, m), 8.52(2H, d, J=4.6) |
| 108 | 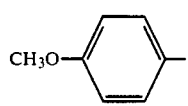 | O | E | oily | 2.85(3H, d, J=4.9), 3.76(3H, s), 3.89(3H, s), 4.97(2H, s), 6.62(1H, brs), 6.82(2H, d, J=9.4), 6.89(2H, d, J=9.4), 6.83-7.33(8H, m) |
| 109 | 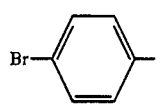 | O | E | oily | 2.84(3H, d, J=4.6), 3.88(3H, s), 4.97(2H, s), 6.65(1H, brs), 6.81(2H, d, J=8.8), 6.87(1H, m), 6.97(1H, d, J=7.8), 7.06 (1H, brs), 7.15-7.18(2H, m), 7.27-7.34(3H, m), 7.35(2H, d, J=8.8) |
| 110 | Ph | O | E | oily | 2.84(3H, d, J=4.9), 3.88(3H, s), 5.01(2H, s), 6.63(1H, brs), 6.88-7.34(13H, m) |
| 111 | 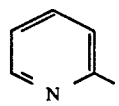 | O | Z | oily | 2.70(3H, d, J=4.9), 3.99(3H, s), 5.35(2H, s), 6.28(1H, brs), 6.79(1H, d, J=8.6), 6.88(3H, m), 7.10(1H, brs), 7.12-7.36 (4H, m), 7.58(2H, brt), 8.15 (1H, dd, J=2.0, 5.1) |
| 112 | Ph | O | Z | oily | 2.76(3H, d, J=4.9), 3.99(3H, s), 5.03(2H, s), 6.29(1H, brs), 6.86-6.99(5H, m), 7.07(1H, brs), 7.12-7.37(6H, m), 7.60(1H, dd, J=1.7, 7.6) |

EXAMPLE 44

Production of N-methyl-2-(2-(Z)-styrylphenyl)-2-(E)-methoxyiminoacetamide (Compound No. 113)

(1) Following the procedure in Example 15, methyl-2-(2-styrylphenyl)-2-(E)-methoxyiminoacetate was prepared from a mixture, i.e. cis- and trans-isomer, of 2-bromostilbene.

(2) To a solution of thus prepared methyl-2-(2-styrylphenyl)-2-(E)-methoxyiminoacetate (0.70 g) in methanol (2 ml), 40 % methanolic methylamine (3 ml) was added, and the resultant mixture was stirred at room temperature for 4 hours. The solvent was removed and the residue was purified by silica gel column chromatography to give 0.26 g of the objective compound, and the mixture (0.45 g) of the objective compound and its isomer, i.e. N-methyl-2-(2-(E)-styrylphenyl)-2-(E)-methoxyiminoacetamide.

EXAMPLE 45

Production of N-methyl-2-(2-(E)-styrylphenyl)-2-(E)-methoxyiminoacetamide (Compound No. 114)

To a solution of N-methyl-2-(2-(Z and E)-styrylphenyl)-2-(E)-metoxyiminoacetamide (0.19 g) in toluene (3 ml), iodine (20 mg) was added, and the resultant mixture was heated under reflux for 20 hours. The solvent was removed and the residue was purified by silica gel column chromatography to give 0.19 g of the objective compound.

EXAMPLE 46

Production of (E)-N-methyl-2-[2'-((1"S*,2"R*)-1",2"-epoxy-2"-phenylethyl) phenyl]-2-methoxyiminoacetamide (Compound No. 115)

To a solutiion of N-methyl-2-(2-(Z)-styrylphenyl)-2-(E)-methoxyiminoacetamide (0.26 g) in dichloromethane (5 ml), m-chloroperbenzoic acid (0.22 g) was added, and the resultant mixture was stirred at room temperature for 3 hours. The reaction mixture was diluted with ether and washed with aqueous sodium thiosulfate. The solvent was dried and removed, and the residue was purified by silica gel column chromatography to give 0.22 g of the objective compound.

EXAMPLE 47

Production of (E)-N-methyl-2-[2'-((1"R*,2"R*)-1",2"-epoxy-2"-phenylethyl) phenyl]-2- methoxyiminoacetamide (Compound No. 116)

In the same manner as in Example 45, the objective compound was prepared from N-methyl-(2-(E)-styrylphenyl)-2-(E)-methoxyiminoacetamide.

EXAMPLE 48

Production of (E)-N-methyl-2-(2-phenylethyl-phenyl)-2-methoxyiminoacetamide (Compuond No. 117)

To a solution of N-methyl-2-(2-(E and Z)-styrylphenyl)-2-(E)-methoxyiminoacetamide or its isomer (0.30 g) in THF (5 ml), 10 % palladium-carbon (0.03 g) was added, and the resultant mixture was stirred at room temperature for 1 hour under hydrogen atmosphere. The reaction mixture was filtered, and the solvent was removed. The residue was purified by silica gel column chromatography to give 0.29 g of the objective compuond.

In the same manner as above, Compounds Nos. 113 to 119 as shown in Table 10 below were obtained.

TABLE 10

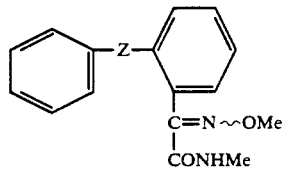

| Compound No. | Z | Steric configuration | m.p. (°C.) | $^1$H—NMR δ (CDCl$_3$) (ppm) |
|---|---|---|---|---|
| 113 | cis-CH=CH- | E | 165–166 | 2.94(3H, d, J=4.9), 3.95(3H, s), 6.78(1H, brs), 6.88(1H, d, J=15.6), 6.88(1H, d, J=15.6), 7.04(1H, d, J=15.6), 7.16-7.46(8H, m), 7.74(1H, d, J=6.8) |
| 114 | trans-CH=CH- | E | 94–95 | 2.89(3H, d, J=5.9), 3.84(3H, s), 6.44 and 6.55(each 1H, ABq, J=11.7), 6.64(1H, brs), 7.15–7.29(9H, m) |
| 115 | epoxide -CH(O)CH- | E | oily | 2.88(3H, d, J=4.9), 3.93(3H, s), 4.22(1H, d, J=3.9), 4.29 (1H, d, J=3.9), 6.54(1H, brs), 7.04–7.23(9H, m) |

TABLE 10-continued

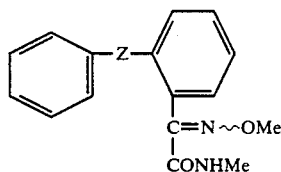

C=N~OMe
|
CONHMe

| Compound No. | Z | Steric configu- ration | m.p. (°C.) | $^1$H—NMR δ (CDCl$_3$) (ppm) |
|---|---|---|---|---|
| 116 | H<br>""\\<br>C——O——C<br>/    ""<br>H | E | 164–166 | 2.82(3H, d, J=5.1), 3.66(1H, d, J=2.0), 3.72(3H, s), 3.76 (1H, d, J=2.0), 6.67(1H, brs), 7.20(1H, d, J=7.3), 7.30– 7.46(8H, m) |
| 117 | —CH$_2$CH$_2$— | E | 130–131 | 2.70–2.87(4H, m), 2.92(3H, d, J=5.1), 3.95(3H, s), 6.72 (1H, brs), 7.08–7.33(9H, m) |
| 118 | —CH(OH)— | E | 102–103 | 2.89(3H, brd), 3.92(3H, brs), 5.67(1H, brs), 7.06–7.39(10H, m) |
| 119 | —CO— | E | oily | 2.85(3H, d, J=4.9), 3.76(3H, s), 6.75(1H, brs), 7.42–7.81 (9H, m) |

Some examples for production of methyl-2-(2-phenoxyphenyl)-2-oxo-acetate, which is the intermediate compound for methyl-2-(2-phenoxyphenyl)-2-methoxyiminoacetamide, are as follows:

REFERENCE EXAMPLE 1

(1) 85% Potassium hydroxide powders (2.18 g; 0.033 mol, 1.1 equimolar amount) were added to phenol (4.23 g; 0.045 mol, 1.5 eq.) under heating, and 1,2-dichlorobenzene (4.41 g; 0.03 mol) and coper(I) iodide (0.29 g; 0.0015 mol) were added thereto, followed by stirring at 160° C. for 24 hours. The reaction mixture ws diluted with water and extracted with ether. The extract was dried over anhydrous magnesium sulfate and concentrated under reduced pressure. The residue was purified by silica gel column chromatography with a mixture of benzene and n-hexane to give 3.48 g (yield, 56.7%) of 2-chlorodiphenyl ehter as colorless crystals. m.p., 33° to 41° C.

(2) A mixture of magnesium (0.49 g; 0.02 mol) in dry THF (3 ml) and a slight amount of iodide was heated at 60° C. for 5 minutes under argon stream, and a mixture of 2-chlorodiphenyl ether as above obtained (2.05 g; 0.01 mol) and dry THF (12 ml) was dropwise added thereto at 50 to 60° C. in 10 minutes, followed by refluxing for 6 hours. The reaction mixture was dropwise added to a solution of dimethyl oxalate (1.18 g; 0.015 mol) in dry THF (15 ml) at not more than -3° C in 2 minutes, followed by stirring at room temperature overnight. An aqueous ammonium chloride solution was poured into the reaction mixture, which was extracted with ether. The extract was washed with water, dried over anhydrous magnesium sulfate and concentrated under reduced pressure. The residue was purified by silica gel column chromatography with a mixture of ethyl acetate and n-hexane to give 1.70 g (yield, 66.4%) of the objective compound as a colorless oil.

REFERENCE EXAMPLE 2

(1) To a mixture of 2-phenoxybenzoic acid (7.71 g; 0.036 mol) dry benzene (80 ml), thionyl chloride (4.76 g; 0.04 mol) and DMF (2 drops) were added, and the resultant mixture was stirred under reflux for 2 hours. The reaction mixture was dropwise added to dry ethanol (100 ml) under ice-cooling in 30 minutes, followed by allowing to stand overnight. The reaction mixture was concentrated under reduced pressure and, after addition of a 4% aqueous sodium hydrogen carbonate solution (150 ml) thereto, extracted with methylene chloride. The extract was dried over anhydrous magnesium sulfate and concentrated under reduced pressure to give ethyl-2-phenoxybenzoate (8.72 g, yield, 100%) as a colorless oil.

(2) To a mixture of magnesium (2.19 g; 0.09 mol), dry benzene (36 ml) and dry THF (14.5 ml), methyl iodide (12.77 g; 0.09 mol) was added under ice-cooling for 2 minutes, followed by stirring at room temperature for 1 hour. To the resultant mixture, triethylamine (27.32 g; 0.27 mol) and a solution of ethyl 2-phenoxybenzoate as above obtained (8.72 g; 0.036 mol) in dry benzene (36 ml) were added at not more than 10° C. for 40 minute, followed by stirring at 10° C. for 4 hours. The reaction mixture was combined with ether (400 ml), washed with a 4% aqueous hydrochloric acid solution (300 ml) and a 4% aqeous sodium hydrogen carbonate solution (300 ml), dried over anhydrous magensium sulfate and concentrated under reduced pressure. The residue was purified by silica gel column chromatography with a mixture of benzene and n-hexane to give 3.82 g (yield, 50.0%) of 2-phenoxyacetophenone as a pale brown oil.

(3) To a solution of 2-phenoxyacetophenone obtained in (2) above (2.12 g; 0.01 mol) in dry methanol (2 ml) and dry chlroform (18 ml), bromide (1.60 g; 0.01 mol) was added at 40° C. in 5 minutes, and the resultant mixture was stirred at room temperature for 30 minutes. The reaction mixture was combined with water (100 ml), extracted with methylene chloride, dried over anhydrous magnesium sulfate and concentrated under reduced pressure to give 3.02 g (yield, 102.3%) of alpha-bromo-2-phenoxyacetophenone as a pale brown oil.

(4) The thus obtained alpha-bromo-2-phenoxyacetophenone (1.18 g; 0.004 mol) was added to a mixture of selenium dioxide (0.49 g; 0.0044 mol) and dry methanol (4 ml) under reflux, and the resultant mixture was stirred under reflux for 18 hours. Insoluble materials were removed by filtration, and the filtrate was concentrated under reduced pressure. The residue was purified by silica gel column chromatography with a mixture of ethyl acetate and n-hexane to give 0.76 g (yield, 74.1%) of methyl-2-(2-phenoxyphenyl)-2-oxoacetate as a colorless oil.

Practical embodiments of the fungicidal composition according to the invention are illustratively shown in the following Formulation Examples wherein part(s) are by weight. The compound number as the active ingredient corresponds to the one in Tables 1 to 10 supra.

PREPARATION EXAMPLE 1

Two parts of Compound No. 3 and 98 parts of talc are mixed well and pulverized to obtain powders.

PREPARATION EXAMPLE 2

Forty parts of Compound No. 3, 10 parts of sodium lignin sulfonate and 50 parts of water are mixed well to obtain a dispersion.

PREPARATION EXAMPLE 3

Ten parts of Compound No. 3, 1 part of Tween 20 ® and 89 parts of isopropanol are mixed well to obtain a solution.

PREPARATION EXAMPLE 4

Fifty parts of Compound No. 4, 6 parts of alkylbezenesulfonate, 4 parts of sodium lignin sulfonate and 40 parts of clay are mixed well and pulverized to obtain a wettable powder.

PREPARATION EXAMPLE 5

Five parts of Compound No. 3, 90 parts of an equilibrated mixture of bentonite and talc and 5 parts of alkylbenzene sulfonate are mixed well and pulverized to obtain granules.

PREPARATION EXAMPLE 6

Twenty-five parts of Compound No. 1, 8 parts of polyoxyalkylphenyl ether, 2 parts of alkylbenzene sulfonate and 65 parts of xylene are dissolved to obtain an emulsifiable concentrate. Typical biological data indicating the excellent fungicidal activity of the compounds of the invention are shown in the following Test Examples wherein a preparation containing methyl-2-phenoxy-phenyl-2-methoxy iminoacetate (JP-A-63-023852, EP-A-0254426) as the active compound is used for comparison, which is hereinafter referred to as "known compound".

(1) Controlling Effect on Plant Diseases by Foliar Treatment (Pot Experiment)

Experiment 1

Controlling effect on *Pyricularia oryzae*:

Two-week rice seedlings (var.: AICHIASAHI) were transplanted in plastic cups (each 9 cmφ) and cultivated another 2 weeks. The test compound in the form of a solution or a suspension was sprayed to the foliage of the rice seedlings, to which a conidia suspension of *Pyricularia oryzae* cultured in an oatmeal medium was inoculated by spraying. The test plant was kept in a moist chamber (28° C. 100% R.H.) for 24 hours, followed by cultivation in a greenhouse for 5 days. Six days after inoculation, the number of lesion of the plant was assessed and the percent control, i.e. preventive effect and curative effect, was calculated as follows: Unless otherwise specifically mentioned, the preventive effect is determined by spraying a designated preparation to the test plant and inoculating the pathogenic fungi thereto after 24 hours, followed by evaluation. The curative effect is determined by inoculating the pathogenic fungi to the test plants and spraying the designated preparation to the plant at the time of slight disease symptoms being observed, i.e. 24 to 48 hours after inoculation, followed by evaluation. The designated preparation herein is the one obtained by dissolving the active compound in a small amount of N,N-dimethylformamide and diluting with water containing a spreading agent to a desired concentration. The percent control was calculated on the following equation:

$$\text{Percent control (\%)} = \frac{\substack{\text{Severity or number of} \\ \text{lesion in untreated plot}} - \substack{\text{Severity or number of} \\ \text{lesion in treated plot}}}{\substack{\text{Severity or number of} \\ \text{lesion in untreated plot}}} \times 100$$

The results are shown in Table 11.

TABLE 11

| | Controlling effect on *Pyricularia oryzae* | | |
|---|---|---|---|
| | Percent control (%) | | |
| | Preventive effect | | Curative effect |
| Compound No. | 125 ppm | 500 ppm | 125 ppm |
| 1 | 50 | 97 | |
| 3 | 97 | 97 | 97 |
| 4 | 50 | 90 | 90 |
| 5 | 30 | 97 | 50 |
| 6 | 97 | 100 | 97 |
| 7 | 50 | 90 | 50 |
| 8 | 90 | 97 | 97 |
| 16 | 90 | 90 | 90 |
| 17 | 70 | 90 | 70 |
| 19 | | 70 | |
| 21 | | 70 | |
| 22 | 70 | 90 | 90 |
| 29 | | 70 | |
| 33 | 97 | 90 | 90 |
| 36 | 97 | 97 | 90 |
| 39 | 97 | 90 | 97 |
| 41 | 97 | 97 | 97 |
| 46 | 90 | 90 | 97 |
| 47 | 90 | 90 | 90 |
| 48 | 90 | 90 | 90 |
| 49 | 90 | 90 | 90 |
| 50 | 90 | 97 | 90 |
| 51 | 90 | 97 | 97 |
| 54 | 70 | 90 | 70 |
| 55 | 90 | 97 | 97 |
| 57 | 90 | 97 | 90 |
| 58 | 90 | 90 | 97 |
| 59 | 70 | 90 | 50 |
| 60 | 97 | 97 | 90 |
| 63 | | 70 | |
| 64 | 50 | 97 | 97 |
| 65 | 90 | 90 | 97 |
| 66 | 70 | 97 | 97 |
| 67 | 70 | 90 | 70 |
| 71 | 30 | 97 | 90 |
| 72 | 50 | 97 | 70 |
| 73 | 70 | 97 | 70 |
| 75 | 50 | 97 | 50 |
| 82 | 70 | 90 | 97 |
| 84 | 97 | 90 | 90 |
| 85 | 50 | 90 | 70 |
| 86 | 90 | 90 | 97 |
| 87 | 90 | 90 | 90 |
| 88 | | 70 | |

TABLE 11-continued

| | Controlling effect on Pyricularia oryzae | | |
|---|---|---|---|
| | Percent control (%) | | |
| | Preventive effect | | Curative effect |
| Compound No. | 125 ppm | 500 ppm | 125 ppm |
| 97 | | 70 | |
| 98 | | 70 | |
| 103 | | 70 | |
| 104 | 70 | 90 | 90 |
| 105 | 70 | 97 | 97 |
| 108 | | 70 | |
| 109 | | 70 | |
| 110 | 97 | 97 | 97 |
| 113 | 70 | 90 | 97 |
| Known compound | | 0 | |

Experiment 2

Controlling effect on *Rhizoctonia solani*:

Two-week rice seedlings (var.: AICHIASAHI) were transplanted in plastic cups (each 9 cmφ) and cultivated another 2 weeks. The test compound in the form of a solution or a suspension was sprayed to the sheath and foliage of the rice seedlings. Mycelia of *Rhizoctonia solani*, which were previously cultivated on the rice bran medium, were put at the feet of the seedlings, and the plant was kept in a moist chamber (28° C., 100% R.H.) for 5 days. The infectious state of the plant was assessed by measuring the height of the mycelia raised along the leaf sheath, and the prercent control was calculated in the same manner as in Experiment 1. The results are shown in Table 12.

TABLE 12

| | Controlling effect on Rhizoctonia solani |
|---|---|
| Compound No. | Preventive effect at 500 ppm (%) |
| 3 | 70 |
| 4 | 50 |
| 6 | 90 |
| 7 | 70 |
| 8 | 70 |
| 16 | 50 |
| 19 | 70 |
| 22 | 70 |
| 41 | 70 |
| 46 | 90 |
| Known compound | 0 |

Experiment 3

Controlling effect on *Sphaerotheca fuliginea*:

Seeds of cucumber (var.: TSUKUBASHIROIBO) were sown in plastic cups (each 9 cmφ), followed by cultivation for 2 to 3 weeks. The test compound in the form of a solution or suspension was sprayed to the surface of their first leaves, and a conidia suspension of *Sphaerotheca fuliginea* cultured on the cucumber leaves was sprayed thereto, and the plants were kept in a greenhouse at 20° C. for 10 days. The controlling effect was assessed by observing the infected area on the leaves and calculated in the same manner as in Experiment 1. The results are shown in Table 13.

TABLE 13

| | Controlling effect on Sphaerotheca fuliginea | | |
|---|---|---|---|
| | Percent control (%) | | |
| | Preventive effect | | Curative effect |
| Compound No. | 125 ppm | 500 ppm | 125 ppm |
| 3 | 100 | 100 | 100 |
| 4 | 100 | 100 | 97 |
| 5 | 100 | 100 | 100 |
| 6 | 100 | 100 | 100 |
| 7 | 100 | 100 | 100 |
| 8 | 100 | 100 | 100 |
| 11 | | 70 | |
| 16 | 100 | 100 | 100 |
| 17 | 100 | 100 | 100 |
| 19 | 100 | 100 | 98 |
| 21 | | 70 | |
| 22 | 100 | 100 | 100 |
| 28 | 90 | 97 | 95 |
| 29 | 100 | 100 | 100 |
| 30 | | 70 | |
| 31 | 100 | 100 | 100 |
| 32 | 100 | 97 | 90 |
| 33 | 100 | 100 | 98 |
| 34 | 100 | 100 | 100 |
| 35 | 70 | 97 | 50 |
| 36 | 100 | 100 | 100 |
| 39 | 100 | 100 | 100 |
| 41 | 100 | 100 | 100 |
| 44 | | 70 | |
| 46 | 97 | 100 | 100 |
| 47 | 100 | 100 | 100 |
| 48 | 100 | 100 | 100 |
| 49 | 100 | 100 | 100 |
| 50 | 100 | 100 | |
| 51 | 100 | 100 | 100 |
| 57 | 100 | 100 | 100 |
| 58 | 100 | 100 | 100 |
| 59 | 100 | 100 | 100 |
| 60 | 100 | 100 | 100 |
| 62 | 100 | 100 | 100 |
| 64 | 100 | 100 | 100 |
| 65 | 100 | 100 | 100 |
| 66 | 100 | 100 | 100 |
| 67 | 100 | 100 | 100 |
| 71 | 100 | 100 | 100 |
| 72 | 85 | 90 | 100 |
| 73 | 100 | 100 | 100 |
| 75 | 100 | 100 | 100 |
| 82 | 100 | 97 | 100 |
| 84 | 100 | 100 | 100 |
| 85 | 100 | 100 | 75 |
| 86 | | 70 | |
| 87 | 100 | 100 | 100 |
| 88 | 100 | 100 | 100 |
| 89 | | 70 | |
| 90 | 100 | 100 | 90 |
| 97 | 100 | 100 | 100 |
| 103 | 70 | 100 | 80 |
| 105 | 100 | 100 | 100 |
| 107 | 80 | 97 | 80 |
| 108 | 100 | 100 | 100 |
| 109 | 100 | 100 | 100 |
| 110 | 100 | 100 | 100 |
| known compound | 100 | 100 | 100 |

Experiment 4

Controlling effect on *Pseudoperonospora cubensis*:

The seeds of cucumber (var.: TSUKUBASHIROIBO) were sown in plastic cups (9 cmφ), followed by cultivation for 2 to 3 weeks. The test compound in the form of a solution or suspension was sprayed to the surface of their first leaves. A zoosporangia suspension of *Pseudoperonospora cubensis* cultured on the cucumber leaves was dropped to the under surface (untreated side) of the leaves, and the plants were cultivated in a greenhouse at 20° C. for 10 days.

The controlling effect was assessed by observing the infected area on the leaves and calculated in the same manner as in Experiment 1. The results are shown in Table 14.

TABLE 14

Controlling effect on *Pseudoperonospora cubensis*

| Compound No. | Preventive effect at 500 ppm (%) |
|---|---|
| 3 | 100 |
| 6 | 70 |
| 8 | 70 |
| 16 | 70 |
| 31 | 70 |
| 33 | 70 |
| 39 | 70 |
| 41 | 70 |
| 46 | 70 |
| 47 | 70 |
| 48 | 70 |
| 50 | 70 |
| 51 | 70 |
| 58 | 70 |
| 64 | 100 |
| 65 | 100 |
| 66 | 100 |
| 71 | 70 |
| 72 | 100 |
| 75 | 70 |
| 103 | 97 |
| 105 | 100 |
| 107 | 70 |
| 110 | 70 |
| Known compound | 0 |

Experiment 5

Controlling effect on *Botrytis cinerea*:

The seeds of cucumber (var.: TSUKUBA-SHIROIBO) were sown in plastic cups (9 cmϕ), followed by cultivation for 2 to 3 weeks. The test compound in the form of a solution or suspension was sprayed to the surface of their first leaves, and the cucumber seedlings were inoculated with mycelial disks (4 mmϕ) of *Botrytis cinerea* cultured on the potato sucrose agar medium by putting the disks on the leaf surfaces. The plants were cultivated in a moist chamber at 20° C. for 2 days. The percent control was assessed by measuring the diameter of the lesions on the leaves and calculated in the same manner as in Experiment 1. The results are shown in Table 15.

TABLE 15

Controlling effect on *Botrytis cinerea*

| Compound No. | Preventive effect 500 ppm | Curative effect 500 ppm |
|---|---|---|
| 3 | 96 | 94 |
| 5 | 50 | 93 |
| 6 | 74 | 95 |
| 7 | 71 | 93 |
| 8 | 68 | 93 |
| 9 | 50 | 74 |
| 11 | 70 | 89 |
| 15 | 59 | 94 |
| 16 | 100 | 94 |
| 17 | 100 | 95 |
| 19 | 74 | 90 |
| 20 | 51 | 82 |
| 21 | 70 | 92 |
| 22 | 90 | 92 |
| 29 | 100 | 98 |
| 31 | 100 | 94 |
| 32 | 100 | 93 |
| 33 | 100 | 95 |
| 34 | 100 | 98 |
| 35 | 50 | |
| 36 | 97 | 96 |
| 39 | 100 | 87 |
| 41 | 70 | 83 |
| 45 | 71 | 51 |
| 46 | 100 | 94 |
| 47 | 70 | 54 |
| 48 | 70 | 96 |
| 49 | 70 | 97 |
| 50 | 72 | 92 |
| 51 | 86 | 94 |
| 53 | 63 | 86 |
| 55 | 79 | 96 |
| 56 | 50 | |
| 57 | 74 | 93 |
| 58 | 90 | 93 |
| 59 | 70 | |
| 60 | 70 | 95 |
| 61 | 50 | |
| 62 | 70 | 96 |
| 63 | 50 | |
| 64 | 70 | 92 |
| 65 | 70 | 94 |
| 66 | 90 | 99 |
| 67 | 70 | 94 |
| 71 | 70 | 95 |
| 72 | 90 | 94 |
| 73 | 90 | 98 |
| 75 | 62 | 96 |
| 82 | 50 | |
| 84 | 50 | |
| 85 | 62 | 86 |
| 86 | 58 | 81 |
| 87 | 63 | 92 |
| 88 | 70 | 68 |
| 89 | 50 | |
| 90 | 69 | 71 |
| 91 | 60 | 86 |
| 92 | 59 | 77 |
| 94 | 50 | |
| 95 | 70 | 62 |
| 97 | 70 | |
| 98 | 50 | |
| 103 | 70 | |
| 104 | 70 | |
| 105 | 100 | |
| 107 | 50 | |
| 108 | 66 | 90 |
| 109 | 42 | 86 |
| 110 | 93 | 94 |
| 113 | 86 | 94 |
| Known compound | 100 | 65 |

The preparations comprising the compounds according to the invention showed in all tested diseases the controlling effect as equal to, or remarkably higher than the known compound, so that their fungicidal activity was confirmed to be higher and their fungicidal spectrum was broader than those of the known compound.

Various compounds, which have been conventionally used as agricultural fungicides such as Captan and Dithane having a broad fungicidal spectrum but not systemic, are useful. However, their fungicidal activity is only exerted on treatment before infection, and any systemic activity during the growth of plants is hardly expected and are thus called the protective fungicides. On the other hand, the compounds of the invention not only have a broad fungicidal spectrum over the wide range of the pathogenic fungi but also possess a high systemic activity. Thus, the compounds according to the invention are useful in protecting the agricultural plants from the attack of the pathogenic fungi with remarkable preventive and curative effects.

(2) Controlling Effect on *Pyricularia oryzae* by Paddy Water Application (Pot Experiment)

Experiment 6

Preventive effect on *Pyricularia oryzae*:

Seeds of rice plant (var.: AICHIASAHI) were sowed in plastic cups (9 cmφ) and cultivated in a greenhouse at 28° C. for 9 days. The test compound dissolved in a small amount of acetone was dropped into the flooded cups at a concentration of the active ingredient being 10 ppm. The rice seedling thus treated were further grown in a greenhouse for 7 days. A conidia suspension of *Pyricularia oryzae* cultivated in an oatmeal medium was sprayed to the foliage of the plants, which were kept in a moist chamber (28° C., 100% R.H.) for 24 hours, followed by cultivation in the greenhouse for 4 days. The number of lesions were observed and the percent control was calculated in the same manner as in Experiment 1. The results are shown in Table 16.

TABLE 16

| | Controlling effect on *Pyricularia oryzae* |
|---|---|
| Compound No. | Percent control (%) at 10 ppm |
| 1 | 70 |
| 3 | 97 |
| 4 | 97 |
| 5 | 97 |
| 6 | 100 |
| 7 | 99 |
| 8 | 100 |
| 16 | 97 |
| 17 | 97 |
| 55 | 98 |
| 82 | 99 |
| Known compound | 0 |

It is obvious from the above test results that the compounds of this invention show a remarkable controlling effect by paddy water application in comparison with the known compound. This prominent fungicidal activity is attributable to the uptake of the compound from the root of the plant.

What is claimed is:

1. A compound of the formula:

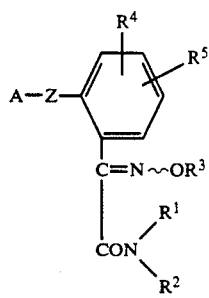

(I)

wherein $R^1$ and $R^2$ are each hydrogen, lower alkyl or cyclo(lower) alkyl; $R^3$ is lower alkyl or cyclo(lower)alkyl; $R^4$ and $R^5$ are each hydrogen, lower alkyl, lower alkoxy, halogen-substituted lower alkyl, lower alkyl-substituted silyl, halogen or nitro; A represents a $C_2$-$C_{12}$ alkenyl group, a $C_2$-$C_{12}$ alkadienyl group, a halogen-substituted $C_2$-$C_{12}$ alkenyl group, a halogen-substituted $C_2$-$C_{12}$ alkadienyl group, a phenyl group or a heterocyclic group selected from the group consisting of pyridyl, pyrimidinyl and pyridazinyl, among which the phenyl group and the heterocyclic group being optionally substituted with not more than three substituents selected from the group consisting of lower alkyl, lower alkanoyl, lower alkyl-substituted silyl, halogen-substituted alkyl, di(lower)alkylamino, phenyl, phenyl(lower)alkyl, phenyl(lower)alkenyl, furyl(lower)alkyl, furyl(lower)alkenyl, halogen, nitro, cyano, —$OR^6$ (in which $R^6$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkylbenzenesulfonyl) and —$CH_2$—$Z'$—$R^7$ (in which $Z'$ is —O—, —S—, —SO— or —NR— (R being hydrogen or lower alkyl) and $R^7$ is phenyl, halophenyl, lower alkoxyphenyl, pyridyl or pyrimidinyl); and Z is —$CH_2$—, —CH(OH)—, —CO—, —O—, —S—, —SO—, —NR— (R being hydrogen or lower alkyl), —$CH_2CH_2$—, —CH=CH—,

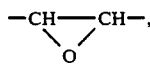

—$CH_2O$—, —$CH_2S$—, —$CH_2SO$—, —$OCH_2$—, —$SCH_2$— or —$SOCH_2$—.

2. A compound of the formula:

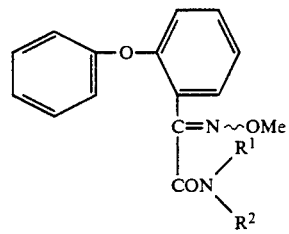

wherein $R^1$ and $R^2$ are each hydrogen or methyl.

3. The compound according to claim 2, wherein $R^1$ is hydrogen and $R^2$ is methyl.

4. A compound of the formula:

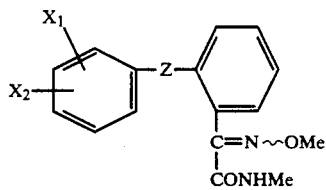

wherein $X_1$ and $X_2$ are each hydrogen, methyl, t-butyl, isopropoxy, cyano, nitro, chlorine, bromine, fluorine, trifluoromethyl, 2-phenylvinyl, benzoyl and dimethylamino and Z is —$OCH_2$—, —$SCH_2$— or —$SOCH_2$.

5. The compound according to claim 1, which has the formula:

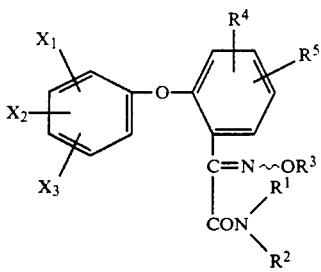
(I-1)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(-lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

6. The compound according to claim 5, wherein $R^1$ is hydrogen, $R^2$ is lower alkyl, $R^3$ is lower alkyl, and $R^4$, $R^5$, $X_1$, $X_2$ and $X_3$ are each as defined in claim 5.

7. The compound according to claim 1, wherein $R^1$ is hydrogen, $R^2$ is lower alkyl, $R^3$ is lower alkyl, $R^4$ is hydrogen, $R^5$ is hydrogen, Z is oxygen and A is phenyl.

8. The compound according to claim 1, wherein $R^1$ is hydrogen, $R^2$ is methyl, $R^3$ is methyl, $R^4$ is hydrogen, $R^5$ is hydrogen, Z is oxygen and A is phenyl.

9. The compound according to claim 1, which has the formula:

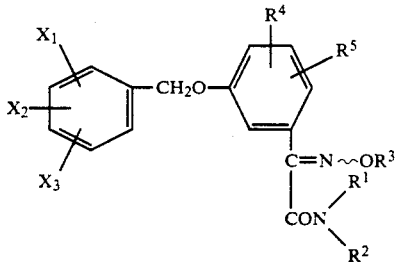
(I-2)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(-lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

10. The compound according to claim 1, which has the formula:

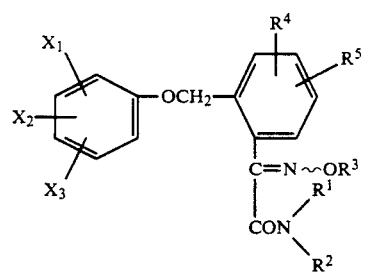
(I-3)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(-lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

11. The compound according to claim 1, which has the formula:

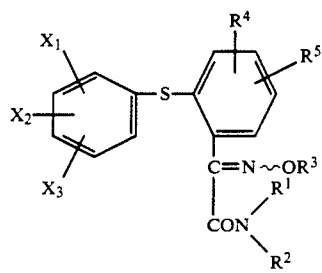
(I-4)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(-lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

12. The compound according to claim 1, which has the formula:

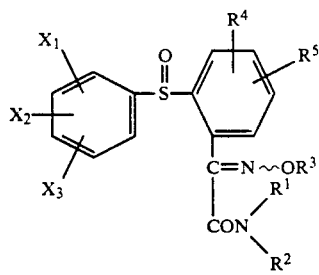
(I-5)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

13. The compound according to claim 1, which has the formula:

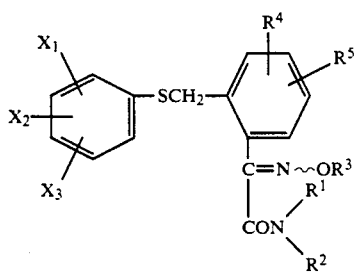
(I-6)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

14. The compound according to claim 1, which has the formula:

(I-7)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro and $X_1$, $X_2$ and $X_3$ are each hydrogen, lower alkyl, lower alkoxy, lower alkanoyl, halogen-substituted lower alkyl, lower alkyl-substituted silyl, halogen, nitro, cyano, di(lower)alkylamino, phenyl, phenyl(lower)alkenyl, furyl(lower)alkenyl, hydroxyl, lower alkynyloxy, lower alkanoyloxy, benzoyloxy, phenoxy, lower alkoxyphenoxy, nitrophenoxy, benzyloxy, cyanobenzyloxy, tetrahydropyranyloxy, pyrimidinyloxy, pyridyloxy, trifluoromethylpyridyloxy, benzothiazolyloxy, quinolyloxy, benzoyl(lower)alkoxy, benzenesulfonyloxy or lower alkylbenzenesulfonyloxy.

15. The compound according to claim 1, which has the formula:

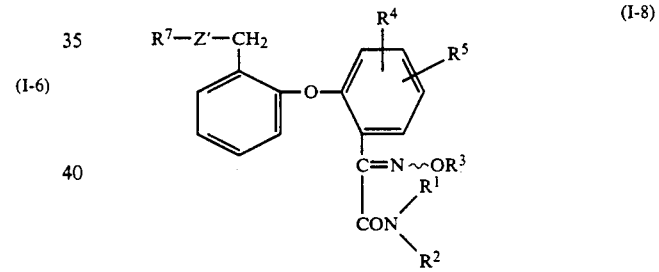
(I-8)

wherein $R^1$ and $R^2$ are each hydrogen or lower alkyl, $R^3$ is lower alkyl, $R^4$ and $R^5$ are each hydrogen, lower alkyl, lower alkoxy, halogen-substituted lower alkyl, lower alkyl-substituted silyl, halogen or nitro, $R^7$ is phenyl, lower alkoxyphenyl, halophenyl, pyridyl or pyrimidinyl and $Z'$ is —O—, —S—, —SO— or —NR— (R being lower alkyl).

16. The compound according to claim 1, which has the formula:

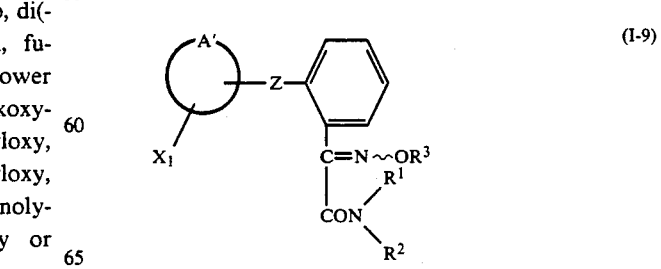
(I-9)

wherein $R^1$ and $R^2$ are each hydrogen or lower alkyl, $R^3$ is lower alkyl,

is pyridyl or pyrimidinyl, Z is —O—, —OCH$_2$— or —CH$_2$O— and X$_1$ is hydrogen or trifluoromethyl.

17. The compound according to claim 1, which has the formula:

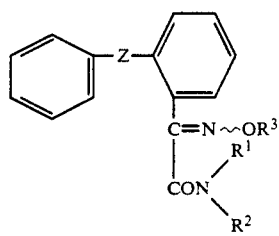

(I-10)

wherein R$^1$ and R$^2$ are each hydrogen or lower alkyl, R$^3$ is lower alkyl and Z is —CH$_2$CH$_2$—,

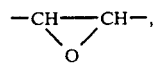

—CH=CH—, —CH(OH)— or —CO—.

18. The compound according to claim 1, which has the formula:

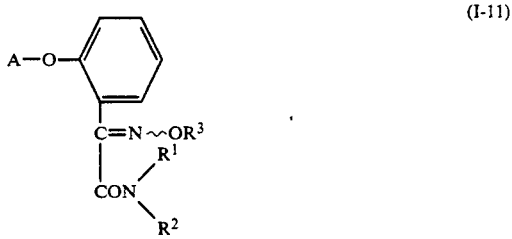

(I-11)

wherein R$^1$ and R$^2$ are each hydrogen or lower alkyl, R$^3$ is lower alkyl and A is alkenyl of 3 to 10 carbon atoms optionally substituted with not more than 3 halogen atoms or alkadienyl of 3 to 10 carbon atoms optionally substituted with not more than 3 halogen atoms.

19. A fungicidal composition which comprises as an active ingredient at least one of the compounds according to claim 1, and an inert carrier or diluent.

20. A method for controlling phytopathogenic fungi which comprises applying as an active ingredient at least one of the compounds according to claim 1 to a locus where phytopathogenic fungi propagate or will propagate.

* * * * *